US007745179B2

(12) United States Patent
McArthur et al.

(10) Patent No.: US 7,745,179 B2
(45) Date of Patent: *Jun. 29, 2010

(54) LENTIVIRAL VECTORS FEATURING LIVER SPECIFIC TRANSCRIPTIONAL ENHANCER AND METHODS OF USING SAME

(75) Inventors: James G. McArthur, San Carlos, CA (US); Dale J. Talbot, San Francisco, CA (US); Andrew D. Simmons, San Mateo, CA (US); Ryan McGuinness, Oakland, CA (US); Michael Kelly, Carlsbad, CA (US); Lisa V. Tsui, Mountain View, CA (US); Thomas Dull, San Francisco, CA (US)

(73) Assignee: GBP IP, LLC, Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/626,192

(22) Filed: Jan. 23, 2007

(65) Prior Publication Data

US 2007/0178592 A1  Aug. 2, 2007

Related U.S. Application Data

(63) Continuation of application No. 10/885,457, filed on Jul. 6, 2004, now Pat. No. 7,179,903, which is a continuation of application No. 10/145,289, filed on May 14, 2002, now Pat. No. 6,808,905.

(60) Provisional application No. 60/291,083, filed on May 14, 2001.

(51) Int. Cl.
C12N 15/64 (2006.01)
C12N 15/00 (2006.01)
C12P 21/06 (2006.01)

(52) U.S. Cl. .................. 435/91.4; 435/69.1; 435/320.1; 435/455

(58) Field of Classification Search ................ 435/69.1, 435/320.1, 455
See application file for complete search history.

(56) References Cited

U.S. PATENT DOCUMENTS

| | | | |
|---|---|---|---|
| 5,583,022 A | 12/1996 | Heidmann et al. |
| 5,614,404 A | 3/1997 | Mazzara et al. |
| 5,650,309 A | 7/1997 | Wong-Staal et al. |
| 5,665,577 A | 9/1997 | Sodroski et al. |
| 5,681,746 A | 10/1997 | Bodner et al. |
| 5,686,279 A | 11/1997 | Finer et al. |
| 5,693,508 A | 12/1997 | Chang |
| 5,716,613 A | 2/1998 | Guber et al. |
| 5,716,826 A | 2/1998 | Gruber et al. |
| 5,739,118 A | 4/1998 | Carrano et al. |
| 5,747,307 A | 5/1998 | Lever et al. |
| 5,750,383 A | 5/1998 | Blissard et al. |
| 5,994,136 A | 11/1999 | Naldini et al. |
| 6,013,516 A | 1/2000 | Verma et al. |
| 6,165,782 A | 12/2000 | Naldini et al. |
| 6,207,455 B1 | 3/2001 | Chang |
| 6,221,349 B1 | 4/2001 | Couto et al. |
| 6,338,953 B1 | 1/2002 | Boyce et al. |
| 6,428,953 B1 | 8/2002 | Naldini et al. |
| 6,808,905 B2 | 10/2004 | McArthur et al. |

FOREIGN PATENT DOCUMENTS

| | | |
|---|---|---|
| WO | WO 98/12314 | 3/1998 |
| WO | WO 99/04026 | 1/1999 |
| WO | WO 99/31251 | 6/1999 |
| WO | WO 00/66759 | 11/2000 |

OTHER PUBLICATIONS

Berkhout et al., "Tat Transactivates the Human Immunodeficiency Virus Through a Nascent RNA Target," Cell, 1989, vol. 59: 273-282.
Blissard et al., "Location, Sequence, Transcriptional Mapping, and Temporal Expression of the gp64 Envelope Glycoprotein Gene of the *Orgyia pseudotsugata* Multicapsid Nuclear Polyhedrosis Virus," Virology, 1989, 170(2): 537-55.
Blomer et al., "Highly Efficient and Sustained Gene Transfer in Adult Neurons with a Lentivirus Vector," Jnl. of Virology, Sep. 1997, vol. 71(9): 6641-6649.
A. Bukovsky et al., "Interaction of Human Immunodeficiency Virus-Derived Vectors with Wild-Type Virus in Transduced Cells," Jnl. of Virology, Aug. 1999, vol. 73(8): 7087-7092.
L-J Chang et al., "Efficacy and Safety Analyses of a Recombinant Human Immunodeficiency Virus Type 1 Derived Vector System," Gene Therapy, 1999, vol. 6: 715-728.
JM Coffin, Fundamental Virology, 1996, $3^{rd}$ Edition (Fields et al., eds), Chapter 26, "*Retroviridae*: The Viruses and Their Replication," pp. 763-843, Lipincott-Raven Publishers, Philadelphia, PA.
R.H. Costa et al., "Transcriptional Control of the Mouse Prealbumin (Transthyretin) Gene: Both Promoter Sequences and a Distinct Enhancer are Cell Specific," Mol. Cell. Biol., 1986, 6: 4697.
M. Curran et al, "Efficient Transduction of Nondividing Cells by Optimized Feline Immunodeficieny Virus Vectors," Mol. Ther., 2000, 1: 31-8.
T. Dull et al., "A Third Generation Lentivirus Vector with a Conditional Packaging System," Jnl. of Virology, Nov. 1998, vol. 72(11): 8463-8471.
Elder et al., "Feline Immunodeficiency Virus as a Model for Development of Molecular Approaches to Intervention Strategies Against Lentivirus infections," Adv. Virus Res., vol. 45: pp. 225-247.
D. Farson et al., "Large-Scale Manufacturing of Safe and Efficient Rerovirus Packaging Lines for Use in Immunotherapy Protocols," Jnl. of Gene Medicine, 1999, vol. 1: 195-209.

(Continued)

Primary Examiner—Maria Leavitt
(74) Attorney, Agent, or Firm—Jones Day

(57) ABSTRACT

Recombinant lentiviruses and transfer vectors for transgene delivery as well as methods for gene therapy using such vectors are disclosed. The invention provides a third generation lentiviral packaging system and a set of vectors for producing recombinant lentiviruses, as well as novel tissue specific enhancer and promoter elements useful for optimizing liver specific transgene delivery. The transgene is preferably a blood clotting factor such as human factor IX (hFIX) or human factor VIII (hFVIII) and can be used for treatment of hemophilia.

28 Claims, 10 Drawing Sheets

OTHER PUBLICATIONS

N. Ferry at al, "Liver-Directed Gene Transfer Vectors," Human Gene Therapy, Sep. 1998, vol. 9: 1975-1981.

Figueiredo et al., "cis-Acting Elements and Transcription Factors Involved in the Promoter Activity of the Human Factor VIII Gene," J. Biol. Chem., 1995, 270: 11828-11838.

M. Gasmi et al., "Requirements for Efficient Production and Transduction of Human Immunodeficiency Virus Type 1-Based Vectors," Jnl. of Virology, Mar. 1999, vol. 73(3): 1828-1834.

Y. Ge at al., "Factors Influencing the Development of an Anti-FIX Immune Response Following Administration of AAV-FIX," Blood, 2001, 97(12): 3733-7.

Ill et al., "Optimization of the Human Factor VIII Complementary DNA Expression Plasmid for Gene Therapy of Hemophilia A," Blood Coagulation Fibrinolysis, 1997, 8: S23-S30.

T. Kafri et al., "A Packaging Cell Line for Lentivirus Vectors," J. Virol., 1999, 73:576-84.

T. Kafri et al., "Sustained Expression of Genes Delivered Directly Into Liver and Muscle by Lentiviral Vectors," Nature Genetics, Nov. 1997, vol. 17: 314-317.

G. Kalpana, "Retroviral Vectors for Liver-Directed Gene Therapy," Seminars in Liver Disease, 1999, vol. 19(1): 27-37.

M.A. Kay, "Hepatic Gene Therapy for Haemophilia B.," Haemophilia, 1998, 4(4): 389-92.

Kim et al., "Construction of Retroviral Vectors with Improved Safety, Gene Expression, and Versatility," Jnl. of Virology, Feb. 1998, vol. 72(2): 994-1004.

N. Klages et al, "A Stable System for the High-Titer Production of Multiply Attenuated Lentiviral Vectors," Molecular Therapy, 2000, 2(2): 170-176.

E. Klimatcheva et al., "Lentiviral Vectors and Gene Therapy," Frontiers in Bioscience, 1999, 4: 481-496.

X. Li et al., "Synthetic Muscle Promoters: Activities Exceeding Naturally Occurring Regulatory Sequences," Nat Biotech., 1999, 17(3): 241-5.

Lisziewicz et al., "Inhibition of Human Immunodeficiency Virus Type 1 Replication by Regulated Expression of a Polymeric Tat Activation Response RNA Decoy as a Strategy for Gene Therapy in AIDS," Proc. Natl. Acad. Sci. USA, 1993, vol. 90: 8000-8004.

H. Miyoshi et al., "Development of a Self-Inactivating Lentivirus Vector," Jnl. of Virology, Oct. 1998, vol. 72(10): 8150-8157.

Monsma et al, "Identification of a Membrane Fusion Domain and an Oligomerization Domain in the Baculovlrus GP64 Envelope Fusion Protein," J. Virol., 1995, 69(4): 2583-95.

L. Naldini et al., "Efficient Transfer, Integration, and Sustained Long-Term Expression of the Transgene in Adult Rat Brains Injected with a Lentiviral Vector," Proc. Natl. Acad. Sci. USA, Oct. 1996, vol. 93: 11382-11388.

L. Naldini et al., "In Vivo Gene Delivery and Stable Transduction of Nondiving Cells by a Lentiviral Vector," Science, Apr. 1996, vol. 272: 263-267.

L. Naldini, "Lentiviruses as Gene Transfer Agents for Delivery to Non-Dividing Cells," Curr. Opin. Biotech., 1998, 9: 457-63.

D. Ory et al., "A Stable Human-Derived Packaging Cell Line for Production of High Titer Retrovirus/Vesicular Stomatitias Virus G Pseudotypes," Proc. Natl. Acad. Sci. USA, Oct. 1996, vol. 93:11400-11406.

F. Park et al., "Efficient Lentiviral Transduction of Liver Requires Cell Cycling In Vivo," Nature Genetics, 2000, 24: 49-52.

F. Park et al., "Therapeutic Levels of Human Factor VIII and IX Using HIV-1-based Lentiviral Vectors in Mouse Liver," Blood, 2000, 96(3): 1173-1176.

Pfeifer, A., et al., "Transduction of liver cells by lentiviral . . . imaging", Molecular Therapy: The J. of Amer. Soc. of Gene Therapy, Mar. 2001, V3, No. 3, pp. 319-322.

Rouet et al, "A Potent Enhancer Made of Clustered Liver-Specific Elements in the Transcription Control Sequences of Human $\alpha$1-Microglobulin/Bikunin Gene," J. Biol. Chem., 1992, 267(29): 20765-20773.

Rouet et al., "Hierarchy and Positive/Negative Interplays of the Hepatocyte Nuclear Factors HNF-1, -3, and -4 in the Liver-Specific Enhancer for the Human $\alpha$-1-Microglobulin/bikunin Precursor," Nucleic Acids Res., 1995, 23(3): 395-404.

Rouet et al., "An Array of Binding Sites for Nepatocyte Nuclear Factor 4 of High and Low Affinities Modulates the Liver-Specific Enhancer for the Human $\alpha_1$-Microglobulin/Bikunin Precursor," Biochem J., 1998, 334: 577-584.

R. Schneider et al., "Inactivation of the Human Immunodeficiency Virus Type I Inhibitory Elements Allows Rev-Independent Expression of Gag and Gag/Protease and Particle Formation," Jnl. of Virology, Jul. 1997, vol. 71(7): 4892-4903.

R. Snyder et al., "Persistant and Therapeutic Concentrations of Human Factor IX in Mice After Hepatic Gene Transfer of Recombinant AAV Vectors," Nat. Genetics, 1997, 16: 270-6.

L.V. Tsui et al., "Production of Human Clotting Factor IX Without Toxicity in Mice After Vascular Delivery of a Lentiviral Vector," Nature Biotechnology, 2002, 20: 53-57.

T. VandenDriessche et al., "Development of ex vivo and in vivo Gene Therapy for Hemophilia A Using Retroviral and Lentiviral Vectors Expressing Factor VIII," Haemostasis, 2000, 30: 5-29.

K. Wion et al., "Distribution of Factor XIII mRNA and Antigen in Human Liver and Other Tissues," Nature, 1985, 317: 726-9.

M.H. Zahler et al., "The Application of a Lentiviral Vector for Gene Transfer in Fetal Human Hepatocytes," Jnl. Gene Med., 2000, 2: 186-193.

M.A. Zern et al., "Hepatic Drug Delivery and Gene Therapy," Hepatology, 1997, 25(2): 484-491.

R. Zufferey et al., "Multiply Attenuated Lentiviral Vector Achieves Efficient Gene Delivery in Vivo," Nature Biotechnology, Sep. 1997, vol. 15: 871-875.

R. Zufferey et al., "Self-Inactivating Lentivirus Vector for Safe and Efficient in Vivo Gene Delivery," Jnl. of Virology, Dec. 1998, vol. 72(12): 9873-9880.

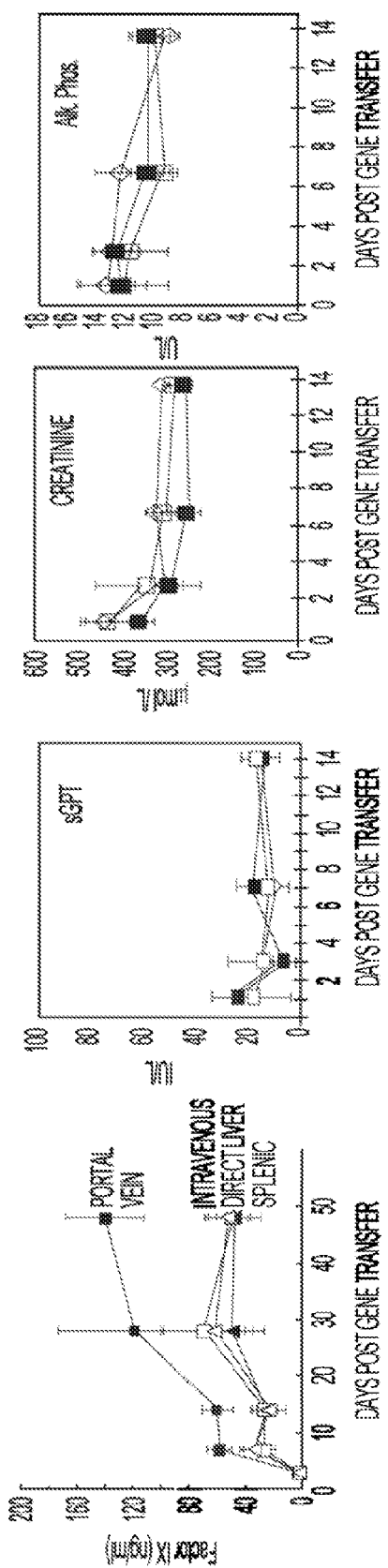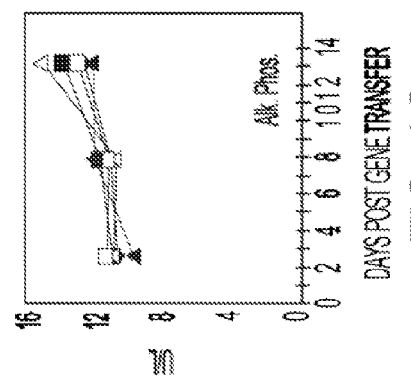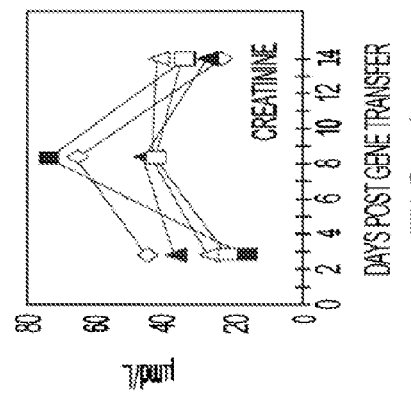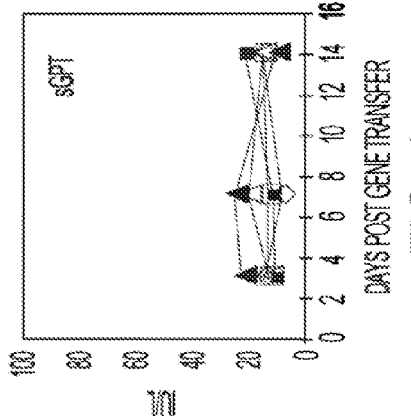

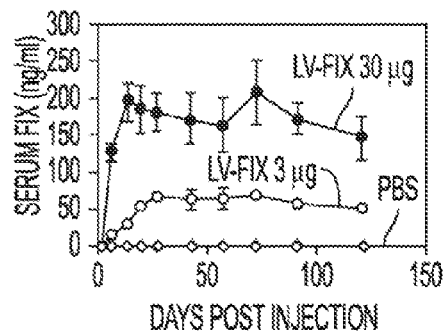
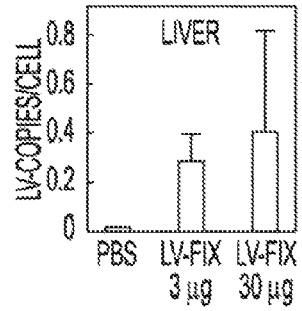
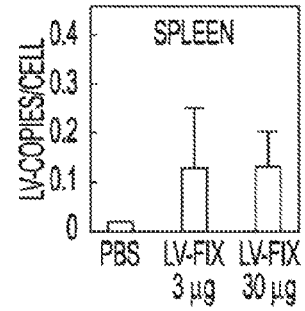
FIG. 6A  FIG. 6B  FIG. 6C
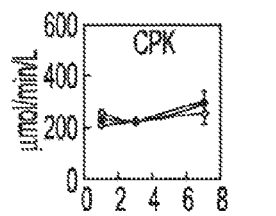
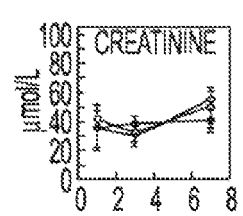
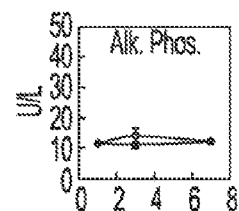
FIG. 6D  FIG. 6E  FIG. 6F
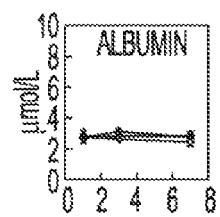
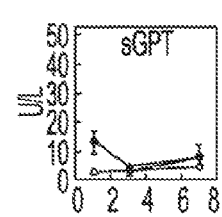
FIG. 6G  FIG. 6H

LENTIVIRAL VECTORS FEATURING LIVER SPECIFIC TRANSCRIPTIONAL ENHANCER AND METHODS OF USING SAME

This application is a continuation of U.S. application Ser. No. 10/885,457, filed Jul. 6, 2004, now U.S. Pat. No. 7,179,903, issued Feb. 20, 2007, which is a continuation of U.S. application Ser. No. 10/145,289, filed May 14, 2002, now U.S. Pat. No. 6,808,905, issued Oct. 26, 2004, which claims benefit of U.S. provisional application No. 60/291,083, filed May 14, 2001, the entire contents of which are incorporated herein by reference.

TECHNICAL FIELD OF THE INVENTION

The present invention relates to gene therapy. In particular it relates to vectors for use in the preparation of recombinant lentiviruses and the use of replication-deficient lentiviral vectors to deliver a therapeutic gene to a target tissue of a subject. Suitable therapeutic genes include genes that encode clotting factors, such as factor VIII or factor IX, to treat a blood clotting disease such as hemophilia. The invention further relates to enhancers and promoters useful for tissue-specific gene therapy.

BACKGROUND OF THE INVENTION

Gene therapy generally relates to the delivery of one or more heterologous genes to a subject in order to treat a disease. Hemophilia is a genetic disease caused by a deficiency of a blood clotting factor. There are two types of X-linked bleeding disorders, hemophilia A and hemophilia B. In some cases of von Willebrand disease, the most common bleeding disorder, deficient levels of vWF result in low levels of factor VIII, mimicking hemophilia A. Hemophilia A affects about 17,000 people in the US and is caused by a deficiency in factor VIII. The incidence of hemophilia B is 1 out of 34,500 men, and it is caused by a deficiency in factor IX. Each of these diseases is an excellent theoretical candidate for gene therapy, as each has a reasonably simple molecular pathology and should be remediable by the delivery of a single gene.

Successful gene therapy for hemophilia requires both tissue specific expression, to avoid a counterproductive immune response, and sufficiently high levels of expression to generate a therapeutic response. Gene therapy directed at quiescent cells of the liver presents an additional challenge, as Park et al. teach that stable and efficient transduction of liver cells with a lentiviral vector requires cell proliferation (Park et al., 2000, Nature Genetics 24:49-52). Park et al. further teach that the injection of doses of the lentiviral vector sufficiently high to reach therapeutic levels of transgene expression in the liver produces a very high liver toxicity and a high mortality (Park et al., 2000, Blood 9(3):1173-1176).

There remains a need for successful gene therapy of quiescent cells that results in therapeutically acceptable cell transduction and that produces a therapeutic amount of protein without toxicity. There is a particular need for a safe and efficient gene therapy for hemophilia.

SUMMARY OF THE INVENTION

The invention is based on the surprising discovery that replication deficient lentiviral vectors can be used to achieve stable genetic modification of cells in vivo without vector-mediated toxicity and in the absence of target cell proliferation. The invention thus provides vectors for transgene delivery as well as methods for gene therapy using such vectors.

The invention further provides promoters and enhancers useful for optimizing tissue specific transgene delivery.

The invention provides a lentiviral producer cell comprising a first nucleotide sequence comprising a gag, a pol, or gag and pot genes; a second nucleotide sequence comprising a heterologous env gene; and a third nucleotide sequence comprising a lentiviral transfer vector that comprises a gene that encodes a blood clotting factor operably linked to an expression control sequence; wherein the producer cell lacks a functional tat gene. In preferred embodiments, the blood clotting factor comprises human factor IX (hFIX) or human factor VIII (hFVIII). In one embodiment, the first, second and third nucleotide sequences are stably integrated into the genome of the lentiviral producer cell. Preferably, the lentivirus is a human immunodeficiency virus (HIV), such as HIV-1. In a preferred embodiment, the producer cell further comprises a fourth nucleotide sequence that comprises a rev gene, and/or lacks functional accessory genes vif, vpr, vpu, vpx and nef, or a combination thereof.

Typically, the expression control sequence comprises a liver specific promoter, such as mouse transthyretin (mTTR) promoter, human alpha-1-antitrypsin promoter (hAAT), human albumin minimal promoter, a human factor VIII endogenous promoter, and/or mouse albumin promoter, and/or a liver specific binding site for transcription, such as EBP, DBP, HNF1, HNF3, HNF4, HNF6, or a combination thereof. Preferably, the expression control sequence comprises an Enh1 enhancer (SEQ ID NO: 10) and an mTTR promoter. Also preferred is an expression control sequence comprising an $\alpha$-1-microglobulin/bikunin enhancer and a human factor VIII endogenous promoter (L-F8).

The invention additionally provides set of lentiviral vectors for use in a third generation lentiviral packaging system and for production of lentiviral producer cells and recombination lentiviruses. The invention provides a lentiviral transfer vector that comprises an expression control sequence operably linked to a transgene, wherein the expression control sequence comprises a novel enhancer element, Enh1 (SEQ ID NO: 10), or a novel combination of enhancer and promoter elements, such as L-F8 or Enh1 and mTTR. The transgene is preferably a therapeutic transgene. A preferred transgene is one that encodes a blood clotting factor, such as human Factor VIII or human Factor IX. Such transgenes encoding blood clotting factors can be used in the treatment of bleeding disorders such as hemophilia. Also provided is a method of producing a lentiviral producer cell comprising transforming a cell with the set of vectors of the invention. The invention further provides a method of producing a recombinant lentivirus, and a method of delivering a transgene to a cell.

BRIEF DESCRIPTION OF THE FIGURES

FIGS. 1A-1H are graphs showing that delivery of LV-hFIX is safe and efficacious. Adult Swiss nude mice received $2 \times 10^8$ TU of LV-HFIX by either portal vein (closed squares), tail vein (open squares), direct intra-splenic (closed triangles) or direct intra-hepatic (open triangles) administration and serum hFIX levels determined by ELISA over time (FIG. 1A). Serum levels of sGPT (FIG. 1B), creatinine (FIG. 1C) and alkaline phosphatase (FIG. 1D) were measured in mice from days 1 to 14 following either portal vein (closed squares) or tail vein (open squares) administration of $2 \times 10^8$ TU of LV-HFIX. This analysis was expanded to include the measurement of serum toxicological markers in Swiss nude mice following administration of $2 \times 10^8$ TU of LV-HFIX by either portal vein (closed squares), tail vein (open squares), direct intra-splenic (closed triangles) or direct intra-hepatic (open triangles) routes, sGPT (FIG. 1E), creatinine (FIG. 1F), alkaline phosphatase (FIG. 1G) and albumin (FIG. 1H). In all figures, the values for the PBS are denoted by the open diamonds.

FIG. 2C: Levels of anti-hFIX antibodies were measured in C57Bl/6 following LV-hFIX vector administration.

FIG. 3A: The average copy number of lentiviral genomes from 4 mice per group. FIG. 3B: The data for two individual portal vein (closed bars) or tail vein (open bars) LV-hFIX mice that expressed 159 ng hFIX/ml serum and 67 ng hFIX/ml serum, respectively, at day 48.

FIGS. 6A-H are graphs showing serum FIX expression following vascular delivery of LV-hFIX. (FIG. 6A) Adult Swiss nude mice received either $1.5\times10^8$ TU (3 µg, ○) or $1.5\times10^9$ TU (30 µg, ●) of LV-hFIX into the portal vein (four mice/group). hFIX levels were determined over time. Animals were killed after 122 days, and vector copy number in the liver (FIG. 6B) and spleen (FIG. 6C) were determined in a subset of animals. Serum levels of creatine phosphokinase (CPK), creatinine, alkaline phosphatase, albumin, and sGPT were determined at various time points immediately after vector administration (FIG. 6D-FIG. 6H, respectively).

FIGS. 9A-9B are liver sections of (FIG. 9A) control and (FIG. 9B) LV-GFP ($4\times10^8$ TU)-transduced mice (n=4) that were analyzed by fluorescence for GFP expression one week after portal vein delivery of LU-GFP. FIG. 9C is a liver section from a third group of four mice that received the LV-GFP after a partial hepatectomy.

FIG. 9D-FIG. 9F show liver sections from a subset of the mice in which BrdU was administered to the mice for seven days after vector administration to identify the cells that had proliferated. BrdU-positive cells are indicated by arrows. FIG. 9G-FIG. 9I show neighboring liver sections that were H & E stained. Scale bar, 10 µm.

FIG. 9J is a bar graph showing the percentage of GFP-positive cells. FIG. 9K is a bar graph showing liver lentiviral copy number: no partial hepatectomy (empty bar), 1.9±0.8 copies/cell; with partial hepatectomy (filled bar), 2.9±1.3 copies/cell. FIG. 9L is a bar graph showing the percentage of BrdU-positive liver cells.

DETAILED DESCRIPTION OF THE INVENTION

Figure 2A:
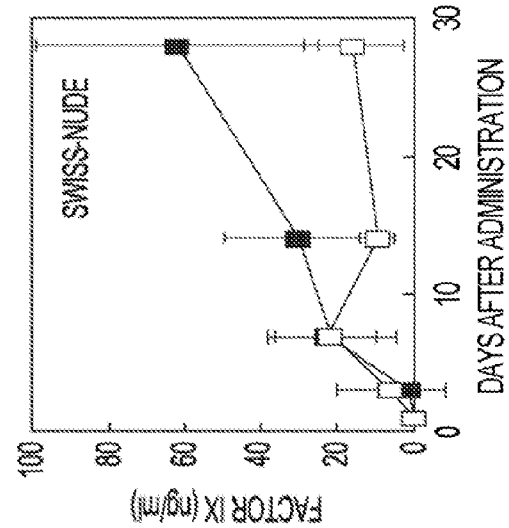
FIGS. 2A-2C are graphs showing delivery of LV-hFIX in immunocompetent mice. Adult Swiss nude (FIG. 2A) and C57Bl/6 (FIG. 2B) mice received $2\times10^8$ TU of LV-hFIX by either portal vein (closed squares) or tail vein (open squares) administration and serum hFIX levels determined by ELISA over time.

The invention is based on the discovery that replication deficient lentiviral vectors can be used to achieve stable genetic modification of cells in vivo without vector-mediated toxicity and in the absence of target cell proliferation. The examples disclosed herein demonstrate that vascular and hepatic delivery of therapeutic doses of a $3^{rd}$ generation lentiviral vector encoding human Factor IX (LV-hFIX) produce serum levels of hFIX with no vector mediated systemic toxicity of adult mice. Vascular delivery of the lentiviral vector results in preferential transduction of the liver and spleen without any concomitant virus-mediated cytopathology. The invention thus provides vectors for transgene delivery as well as methods for gene therapy using such vectors. The invention further provides promoters and enhancers useful for optimizing tissue specific transgene delivery.

DEFINITIONS

All scientific and technical terms used in this application have meanings commonly used in the art unless otherwise specified. As used in this application, the following words or phrases have the meanings specified.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871-875.

As used herein, a "third generation" lentiviral vector system refers to a lentiviral packaging system that has the characteristics of a second generation vector system, and that further lacks a functional tat gene, such as one from which the tat gene has been deleted or inactivated. Typically, the gene encoding rev is provided on a separate expression construct. See, e.g., Dull et al., 1998, J. Virol. 72(11):8463-8471.

As used herein, "packaging system" refers to a set of viral constructs comprising genes that encode viral proteins involved in packaging a recombinant virus. Typically, the constructs of the packaging system will ultimately be incorporated into a packaging cell.

As used herein, a "retroviral transfer vector" or "lentiviral transfer vector" means an expression vector that comprises a nucleotide sequence that encodes a transgene and that further comprises nucleotide sequences necessary for packaging of the vector.

As used herein, "significant toxicity" means a level of toxicity that contraindicates clinical use as determined by an art-accepted measure of toxicity. Examples of art-accepted measures of toxicity include, but are not limited to, elevated serum levels of an enzyme or other substance associated with liver toxicity, such as sGPT, creatinine, alkaline phosphatase and alanine aminotransferase (ALT). In one embodiment, elevated serum levels means higher than the upper limit of the normal range.

As used herein, "subject" refers to the recipient of the therapy to be practiced according to the invention. The subject can be any animal, including a vertebrate, but will preferably be a mammal. If a mammal, the subject will preferably be a human, but may also be a domestic livestock, laboratory subject or pet animal.

As used herein, "transgene" means a polynucleotide that can be expressed, via recombinant techniques, in a non-native environment or heterologous cell under appropriate conditions. The transgene may be derived from the same type of cell in which it is to be expressed, but introduced from an exogenous source, modified as compared to a corresponding native form and/or expressed from a non-native site, or it may be derived from a heterologous cell. "Transgene" is synonymous with "exogenous gene", "foreign gene" and "heterologous gene".

As used herein, a "therapeutic" gene means one that, when expressed, confers a beneficial effect on the cell or tissue in which it is present, or on a mammal in which the gene is expressed. Examples of beneficial effects include amelioration of a sign or symptom of a condition or disease, prevention or inhibition of a condition or disease, or conferral of a desired characteristic. Therapeutic genes include genes that correct a genetic deficiency in a cell or mammal.

As used herein, a "promoter" means a nucleic acid sequence capable of directing transcription.

As used herein, a "therapeutically acceptable amount" of a substance means a sufficient quantity of the substance that an amelioration of adverse symptoms or protection against adverse symptoms can be detected in a subject treated with the substance.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "nucleotide sequence", "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, "a" or "an" means at least one, unless clearly indicated otherwise.

Lentiviral Vectors, Packaging Systems and Producer Cells

The invention provides lentiviral vectors, particles, packaging systems and producer cells capable of producing a high titer recombinant lentivirus capable of selectively infecting human and other mammalian cells. In one embodiment, the recombinant lentivirus of the invention has a titer of $5 \times 10^5$ infectious units/ml. Preferably, the recombinant retrovirus has a titer of $2 \times 10^6$ infectious units/ml, and more preferably, of $1 \times 10^7$ infectious units/ml. Typically, titer is determined by conventional infectivity assay on 293T, HeLa or HUH7 hepatoma cells.

Lentiviruses include members of the bovine lentivirus group, equine lentivirus group, feline lentivirus group, ovinecaprine lentivirus group and primate lentivirus group. The development of lentiviral vectors for gene therapy has been reviewed in Klimatcheva et al., 1999, Frontiers in Bioscience 4: 481-496. The design and use of lentiviral vectors suitable for gene therapy is described, for example, in U.S. Pat. No. 6,207,455, issued Mar. 27, 2001, and U.S. Pat. No. 6,165,782, issued Dec. 26, 2000. Examples of lentiviruses include, but are not limited to, HIV-1, HIV-2, HIV-1/HIV-2 pseudotype, HIV-1/SIV, FIV, caprine arthritis encephalitis virus (CAEV), equine infectious anemia virus and bovine immunodeficiency virus. HIV-1 is preferred.

Also provided is a lentiviral vector that contains a transgene, as well as a pharmaceutical composition comprising the lentiviral vector and, optionally, a pharmaceutically acceptable carrier. The transgene is typically a therapeutic gene. An example of a therapeutic transgene directed at treatment of hemophilia is one that encodes a blood clotting factor, such as a polynucleotide encoding factor VIII or a polynucleotide encoding factor IX. In other examples, the therapeutic gene may be directed at cancer, infectious disease, a genetic deficiency or other condition. Additional examples of therapeutic genes are those that encode cytokines, including interleukins and colony stimulating factors. Those skilled in the art will appreciate a variety of transgenes that are suitable for use with the invention.

In one embodiment, the recombinant lentivirus can be used to transduce cells of a subject without resulting in significant toxicity or immunogenicity in the subject, and, following transduction, the transgene is expressed. Upon transduction of the cells of a subject, the therapeutic protein is expressed in a therapeutically acceptable amount. In some embodiments, the cells to be transduced are non-dividing cells, such as neuronal, muscle, liver, skin, heart, lung and bone marrow cells. In a preferred embodiment, the cells of the subject are liver cells. Typically, the transgene is operatively linked to a promoter or other expression control sequence. An inducible promoter can be used for controlled expression of the transgene.

Expression Control Sequences

In a preferred embodiment, expression of the transgene is under the control of a tissue specific promoter and/or enhancer. Preferably the promoter or other expression control sequence selectively enhances expression of the transgene in liver cells. Examples of liver specific promoters include, but are not limited to, the mouse thyretin promoter (mTTR), the endogenous human factor VIII promoter (F8), human alpha-1-antitrypsin promoter (hAAT), human albumin minimal promoter, and mouse albumin promoter. The mTTR promoter is preferred. The mTTR promoter is described in R. H. Costa et al., 1986, Mol. Cell. Biol. 6:4697. The F8 promoter is described in Figueiredo and Brownlee, 1995, J. Biol. Chem. 270:11828-11838.

Expression levels can be further enhanced to achieve therapeutic efficacy using one or more enhancers. One or more enhancers can be provided either alone or together with one or more promoter elements. Typically, the expression control sequence comprises a plurality of enhancer elements and a tissue specific promoter. A preferred enhancer comprises one or more copies of the α-1-microglobulin/bikunin enhancer (Rouet et al., 1992, J. Biol. Chem. 267:20765-20773; Rouet et al., 1995, Nucleic Acids Res. 23:395-404; Rouet et al., 1998, Biochem. J. 334:577-584; III et al., 1997, Blood Coagulation Fibrinolysis 8-S23-S30). Also preferred are enhancers derived from liver specific transcription factor binding sites, such as EBP, DBP, HNF1, HNF3, HNF4, HNF6, with Enh1, comprising HNF1 (sense)-HNF3 (sense)-HNF4 (antisense)-HNF1 (antisense)-HNF6 (sense)-ESP (antisense)-HNF4 (antisense), being most preferred (see Example 2 below).

As disclosed in Example 4 below, two copies of α-1-microglobulin/bikunin enhancer, also referred to as Enhancer L, in combination with a ~300 nucleotide fragment of the human Factor VIII endogenous promoter (Figueiredo and Brownlee, 1995, J. Biol. Chem. 270:11828-11838), has been shown to provide sustained expression (>14 days) in the HemoA null mouse in vivo. As described in Example 3 below, the combination of Enh1 and the mTTR promoter enhances the activity over the mTTR promoter alone by about two fold.

Packaging Systems

The invention is applicable to a variety of retroviral systems, and those skilled in the art will appreciate the common elements shared across differing groups of retroviruses. The description herein uses lentiviral systems as a representative example. All retroviruses, however, share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by env, and CA (p24), MA (p17) and NC (p7-11), which are encoded by the gag gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated.

First generation lentiviral vector systems provide separate packaging constructs for gag/pol and env, and typically employ a heterologous envelope protein for safety reasons. In second generation lentiviral vector systems, the accessory genes, vif, vpr, vpu and nef, are deleted or inactivated. Third generation lentiviral vector systems are those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each for gagpol, rev, env and the transfer vector. Regardless of the generation of packaging system employed, gag and pol can be provided on a single construct or on separate constructs.

Accordingly, the invention provides a retroviral packaging system that comprises at least two vectors, a first packaging vector comprising a gag, a pol, or gag and pol genes operably linked to an expression control sequence; and a second packaging vector comprising a heterologous env gene operably linked to an expression control sequence. For production of recombinant lentiviral vectors of the invention, the system further comprises a lentiviral transfer vector that comprises a gene that encodes a blood clotting factor operably linked to an expression control sequence. Typically, the set of lentiviral vectors lacks a functional tat gene.

Preferably, the heterologous env gene comprises a VSV-G or baculoviral gp64 env gene, although those skilled in the art will appreciate other suitable env genes. Pseudotyping with a baculoviral env gene, for example, can reduce toxicity and avoid an overly broad tropism that can lead to an undesired immune response directed against the recombinant viral vector. Representative gp64 genes and methods for preparing them are described in Monsma & Blissard, 1995, J. Virol. 69(4):2583-95; Blissard & Rohrmann, 1989, Virology 170 (2):537-55; and Blissard & Monsma, U.S. Pat. No. 5,750, 383. The gp64 or other baculoviral env gene can be derived from *Autographa californica* nucleopolyhedrovirus (AcMNPV), *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, Dhori virus, Thogoto virus, *Antheraea pemyi* nucleopolyhedrovirus or Batken virus. Preferably, the gp64 env gene is an AcMNPV gp64 env gene.

In a preferred embodiment, the retroviral elements are derived from a lentivirus, such as HIV. Preferably, the vectors lack a functional tat gene and/or functional accessory genes (vif, vpr, vpu, vpx, net. In another preferred embodiment, the system further comprises an additional vector that comprises a rev gene.

The vectors of the packaging system are expression constructs that include the gene(s) encoding retroviral packaging elements, wherein each gene is operably linked to an expression control sequence. In one embodiment, the vector is a plasmid. Other vectors, however, are known in the art and include, for example, viral vectors.

Typically, the vectors are included in a packaging cell. The vectors are introduced via transfection, transduction or infection into the packaging cell line. Methods for transfection, transduction or infection are well known by those of skill in the art. A transfer vector can be introduced into the packaging cell line, via transfection, transduction or infection, to create a producer cell. The producer cell produces viral particles that contain the transgene. The recombinant virus is recovered from the culture media and titrated by standard methods used by those of skill in the art.

The packaging constructs can be introduced into human cell lines by calcium phosphate transfection, lipofection or electroporation, generally together with a dominant selectable marker, such as neo, DHFR, Gln synthetase or ADA, followed by selection in the presence of the appropriate drug and isolation of clones. A selectable marker gene can be linked physically to the packaging genes in the construct.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400-11406, which describe packaging cells. Further description of stable cell line production can be found in Dull et al., 1998, J. Virology 72(11):8463-8471; and in Zufferey et al., 1998, J. Virology 72(12):9873-9880

Zufferey et al., 1997, Nature Biotechnology 15:871-875, teach a lentiviral packaging plasmid wherein sequences 3' of pol including the HIV-1 env gene are deleted. The construct contains tat and rev sequences and the 3' LTR is replaced with poly A sequences. The 5 LTR and psi sequences are replaced by another promoter, such as one that is inducible. For example, a CMV promoter or derivative thereof can be used.

The packaging vectors of interest may contain additional changes to the packaging functions to enhance lentiviral protein expression and to enhance safety. For example, all of the HIV sequences upstream of gag can be removed. Also, sequences downstream of env can be removed. Moreover, steps can be taken to modify the vector to enhance the splicing and translation of the RNA.

Optionally, a conditional packaging system is used, such as that described by Dull et al., 1998, J. Virology 72(11):8463-8471. Also preferred is the use of a self-inactivating vector (SIN), which improves the biosafety of the vector by deletion of the HIV-1 long terminal repeat (LTR) as described, for example, by Zufferey et al., 1998, J. Virology 72(12):9873-9880. Inducible vectors can also be used, such as through a tet-inducible LTR.

The techniques used to construct vectors, and to transfect and to infect cells, are practiced widely in the art. Practitioners are familiar with standard resource materials that describe specific conditions and procedures. Construction of the vectors of the invention employs standard ligation and restriction techniques that are well understood in the art (see Maniatis et al., in Molecular Cloning, A Laboratory Manual, Cold Spring Harbor Laboratory, N.Y., 1982). Isolated plasmids. DNA sequences or synthesized oligonucleotides are cleaved, tailored and religated in the form desired.

Conventional methods can be used to propagate the viruses used in the invention (see, e.g., Burleson, et al., 1992, Virology; A Laboratory Manual, Academic Press, Inc., San Diego, Calif.; and Mahy, ed., 1985, Virology, A Practical Approach, IRL Press, Oxford, UK). Conventional conditions for propagating viruses are suitable for allowing expression of a baculoviral envelope protein on the surface of a retrovirus particle used in the invention.

Methods for the large-scale production of safe and efficient retrovirus packaging lines for use in immunotherapy protocols is described in Farson et al., 1999, J. Gene Medicine 1:195-209. Additional guidance on the production and use of lentiviral vectors is provided in U.S. Pat. No. 6,165,782, issued Dec. 26, 2000, and in PCT Application No. US 00/11097, published Nov. 29, 2000. Transduction efficiency can be enhanced and toxicity minimized or eliminated through the selection of elements for the vector construct as well as through vector purification.

Producer cells of the invention comprise packaging constructs as described above, as well as an expression construct that comprises a transgene of interest operably linked to an expression control sequence. This expression construct is also referred to as a transfer vector.

Preferred is the use of recombinant lentiviral vectors that are capable of high infectivity (e.g., more than 20% of target cells expressing transgene, preferably more than 25% of target cells expressing, or an infectivity of at least about $5 \times 10^7$ TU/µg p24 Gag antigen) of quiescent as well as proliferating cells. Also preferred is the use of a purification protocol sufficient to produce a viral stock that is substantially free of non-infectious contaminants. In a preferred embodiment, the vectors are centrifuged at low speed, filtered, and then concentrated by high speed centrifugation, such as at about 19,500 rpm.

Transgenes

The transgene can be any nucleic acid of interest that can be transcribed. Generally the transgene encodes a polypeptide. Preferably the polypeptide has some therapeutic benefit. The polypeptide may supplement deficient or nonexistent expression of an endogenous protein in a host cell, or the polypeptide can confer new properties on the host cell, such as a chimeric signaling receptor (see U.S. Pat. No. 5,359,046). The artisan can determine the appropriateness of a particular transgene by using techniques known in the art. For example, the artisan would know whether a foreign gene is of a suitable size for encapsidation and whether the foreign gene product is expressed properly.

It may be desirable to modulate the expression of a gene-regulating molecule in a cell by the introduction of a molecule by the method of the invention. The term "modulate" refers to the suppression of expression of a gene when it is over-expressed, or to augmentation of expression when it is under-expressed. Where a cell proliferative disorder is associated with the expression of a gene, nucleic acid sequences that interfere with the expression of a gene at the translational level can be used. The approach can utilize, for example, antisense nucleic acid, ribozymes or triplex agents to block transcription or translation of a specific mRNA, either by masking that mRNA with an antisense nucleic acid or triplex agent, or by cleaving same with a ribozyme.

Antisense nucleic acids are DNA or RNA molecules that are complementary to at least a portion of a specific mRNA molecule (Weintraub, 1990, Sci. Am. 262:40). In the cell, the antisense nucleic acids hybridize to the corresponding mRNA, forming a double-stranded molecule. The antisense nucleic acids interfere with the translation of the mRNA, as the cell will not translate a mRNA that is double-stranded. Antisense oligomers of about 15 nucleotides or more are preferred because such are synthesized easily and are less likely to cause problems than larger molecules when introduced into the target cell. The use of antisense methods to inhibit the in vitro translation of genes is well known in the art (Marcus-Sakura, 1988, Anal. Biochem. 172:289).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism and other diseases. Antisense nucleic acids are also useful for the inhibition of expression of proteins associated with toxicity.

Use of an oligonucleotide to stall transcription can be by the mechanism known as the triplex strategy since the oligomer winds around double-helical DNA, forming a three-strand helix. Therefore, the triplex compounds can be designed to recognize a unique site on a chosen gene (Maher et al., 1991, Antisense Res and Dev. 1(3):227; Helene, 1991, Anticancer Drug Dis. 6(6):569).

Ribozymes are RNA molecules possessing the ability to specifically cleave other single-stranded RNA in a manner analogous to DNA restriction endonucleases. Through the modification of nucleotide sequences which encode those RNA's, it is possible to engineer molecules that recognize and cleave specific nucleotide sequences in an RNA molecule (Cech, 1988, J. Amer. Med Assn. 260:3030). A major advantage of that approach is only mRNAs with particular sequences are inactivated.

It may be desirable to transfer a nucleic acid encoding a biological response modifier. Included in that category are immunopotentiating agents including nucleic acids encoding a number of the cytokines classified as interleukins, for example, interleukins 1 through 12. Also included in that category, although not necessarily working via the same mechanism, are interferons, and in particular, gamma interferon (γ-IFN), tumor necrosis factor (TNF) and granulocyte-macrophage colony stimulating factor (GM-CSF). It may be desirable to deliver such nucleic acids to bone marrow cells or macrophages to treat inborn enzymatic deficiencies or immune defects. Nucleic acids encoding growth factors, toxic peptides, ligands, receptors or other physiologically important proteins also can be introduced into specific non-dividing cells.

Thus, the recombinant lentivirus of the invention can be used to treat an HIV-infected cell (e.g., T-cell or macrophage) with an anti-HIV molecule. In addition, respiratory epithelium, for example, can be infected with a recombinant lentivirus of the invention having a gene for cystic fibrosis transmembrane conductance regulator (CFTR) for treatment of cystic fibrosis.

The method of the invention may also be useful for neuronal, glial, fibroblast or mesenchymal cell transplantation, or grafting, which involves transplantation of cells infected with the recombinant lentivirus of the invention ex vivo, or infection in vivo into the central nervous system or into the ventricular cavities or subdurally onto the surface of a host brain. Such methods for grafting are known to those skilled in the art and are described in Neural Grafting in the Mammalian CNS, Bjorklund & Stenevi, eds. (1985).

For diseases due to deficiency of a protein product, gene transfer could introduce a normal gene into the affected tissues for replacement therapy, as well as to create animal models for the disease using antisense mutations. Preferably, the transgene encodes a blood clotting factor, such as Factor VIII or IX, and the target cell is a liver cell.

Methods

The invention provides a method of producing a recombinant lentivirus. The method comprises transforming a host cell with a first nucleotide sequence comprising a gag, a pol, or gag and pol genes; and a second nucleotide sequence comprising a heterologous env gene. Preferably, the env gene comprises a VSV-G or gp64 env gene. In a preferred embodiment, the lentiviral elements are derived from HIV, such as HIV-1. Preferably, the vectors lack a functional tat gene and/or functional accessory genes (vif, vpr, vpu, vpx, nef). In another preferred embodiment, the method further comprises transforming the host cell with an additional nucleotide sequence that comprises a rev gene. The method further comprises transforming the host cell with a transfer vector comprising a transgene operably linked to an expression control sequence. Preferably, the transgene is a therapeutic transgene, such as a transgene that encodes a blood clotting factor (e.g., Factor VIII or Factor IX). Preferred expression control sequences include tissue specific promoters and/or enhancers, such as one of the liver specific promoters or enhancers disclosed herein. The host cell can be cultured under conditions suitable for viral production, and recombinant virus can be recovered from the culture medium.

The invention additionally provides methods for delivering a transgene to a cell, in vivo, in vitro or ex vivo. Also provided are methods of treating a subject and of delivering a therapeutic transgene to cells of a subject. In one embodiment, the subject is treated for hemophilia and the transgene comprises a blood clotting factor. The transgene can be delivered to dividing or to quiescent cells in a subject, such as liver cells. The method comprises transducing a ell with a recombinant lentiviral vector that contains a transgene. Preferably, the transgene is a therapeutic transgene. In a typical embodiment, significant toxicity is not caused in the subject. Toxicity can be minimized or eliminated by use of a vector of the invention, such as those described herein and having an infectivity of at least about $5 \times 10^7$ TU/μg p24 Gag antigen.

Vectors of the invention can be administered to a subject parenterally, preferably intravascularly (including intravenously). When administered parenterally, it is preferred that the vectors be given in a pharmaceutical vehicle suitable for injection such as a sterile aqueous solution or dispersion. Following administration, the subject is monitored to detect changes in gene expression. Dose and duration of treatment is determined individually depending on the condition or disease to be treated. A wide variety of conditions or diseases can be treated based on the gene expression produced by administration of the gene of interest in the vector of the present invention. The dosage of vector delivered using the method of the invention will vary depending on the desired response by the host and the vector used. Generally, it is expected that up to 100-200 μg of DNA or RNA can be administered in a single dosage, although a range of 0.5 mg/kg body weight to 50 mg/kg body weight will be suitable for most applications.

EXAMPLES

The following examples are presented to illustrate the present invention and to assist one of ordinary skill in making and using the same. The examples are not intended in any way to otherwise limit the scope of the invention. Various references are indicated by numbers presented in superscript form. The citations for these references are provided in a list at the conclusion of the Examples.

Example 1

Production of Human Factor IX without Toxicity in Mice after Vascular Delivery of a Lentiviral Vector Replication deficient lentiviral vectors have been shown to enable the stable genetic modification of multiple cell types in vivo. This example demonstrates that vascular and hepatic delivery of therapeutic doses of a $3^{rd}$ generation HIV derived lentiviral vector encoding human Factor IX (LV-hFIX) produce therapeutic serum levels of hFIX protein with no vector mediated local or systemic toxicity of adult mice. Vascular delivery of the lentiviral vector resulted in the preferential transduction of the liver and spleen without any concomitant virus-mediated cytopathology. Cell proliferation was not required for hepatocyte transduction with either a LV encoding hFIX or a LV encoding GFP. Portal vein administration produced the highest serum levels of hFIX and demonstrated proportionally higher levels of gene transfer to the liver with up to 35% of cells, hepatocytes, endothelial cells and Kupffer cells, expressing hFIX. Serum hFIX levels reached 4% of normal levels following vascular LV-mediated hFIX gene transfer and remained stable for months following vector administration.

Introduction

Replication deficient murine MLV based retroviruses have been employed for years in the ex vivo genetic modification of cells as well as in a limited number of in vivo gene therapy protocols. These vectors, while suitable for many applications, have the significant disadvantage of requiring DNA replication and the breakdown of the nuclear membrane that accompanies cell division to stably transduce target cells. Replication deficient lentivirus vectors were developed to overcome this limitation[1]. Unlike MLV based retroviral vectors, lentiviral vectors efficiently transduce both growth arrested and proliferating cells in vitro and in vivo[1-5]. Typical $3^{rd}$ generation lentiviral transfer vectors retain less than 8% of the wild type HIV (wtHIV) sequences and have been deleted of the HIV gag, pol and env genes as well as the HIV accessory genes; vpr, vpu, vif and nef[4,6]. Further deletions in the 3' LTR of the vector have been made to create self-inactivating vectors that do not mobilize following integration into the target cell, even upon subsequent infection with wtHIV[7,8]. The development of lentiviral vector producer cell lines now facilitate the manufacture of large quantities of the vector[9].

Lentiviral vectors have been shown to stably transduce liver, muscle, skin, retina and brain in mice, rats or dogs following vascular, intramuscular, intradermal, intraoccular and intracranial administration respectively[1-5, 10-12]. The cells in several of these tissues are typically in a quiescent state. In contrast with these reports, it has been recently suggested that liver directed delivery of lentiviral vectors does not result in transduction of hepatocytes in the absence of cell division or DNA replication[13,14].

The impact of the route of administration of a $3^{rd}$ generation lentiviral vector on vector biodistribution, hFIX expression and vector safety in adult mice was examined. The vascular administration of $2\times10^8$ transducing units (TU) (4 µg of p24) of a $3^{rd}$ generation VSV-G pseudotyped lentiviral vector encoding human Factor IX (hFIX) in adult Swiss nude mice produced significant stable serum levels of hFIX without any evidence of local or systemic toxicity. Quantitative PCR analysis of 10 tissues indicated that over 80% of vector genomes were found in the liver following intraportal administration of vector. Immunohistochemistry indicated that up to 35% of the hepatocytes and sinusoidal cells expressed the hFIX protein. Peripheral vascular (tail vein) administration of the vector resulted in lower serum levels of hFIX, lower genome copies in the liver, and lower levels of hFIX positive liver cells. There was however an increase in the transduction of the spleen with tail vein administration. These results demonstrate that vascular administration of lentiviral vectors is an efficient and safe means of introducing the FIX gene into the liver.

Results

Safe and Efficient Vascular Delivery of Lentiviral Vector

The liver is the natural site for the expression of numerous secreted proteins including hFIX[17]. Examined here was the efficacy of hFIX gene delivery using a $3^{rd}$ generation VSV-G pseudotyped lentiviral vector encoding hFIX (LV-hFIX) delivered by multiple routes to access the liver. Four µg p24 ($2\times10^8$ TU) of LV-hFIX was administered to adult Swiss nude mice by intraportal vein, intra-tail vein, splenic or direct liver injection (FIG. 1A). hFIX was detected in the serum as soon as 3 days following gene transfer in all mice. In mice that received LV-hFIX by the intraportal route, hFIX levels increased over several weeks following gene transfer and serum hFIX reached peak levels of 170 ng hFIX/ml (FIG. 1A, dosed squares). Serum hFIX levels were lower in mice that received LV-hFIX by the tail vein (FIG. 1A, open squares), splenic (FIG. 1A, closed triangles) or direct liver (FIG. 1A, open triangles) routes reaching maximal levels of 121 ng hFIX/ml.

To ascertain whether the LV-hFIX delivered to the portal vein or tail vein induced any systemic cytopathology, serum samples were tested for elevation of serum markers of toxicity. At alt time points examined, 1, 3, 7 and 14 days following vector administration, sGPT, creatinine and alkaline phosphatase levels were within the normal range and were indistinguishable from the PBS control animals (FIG. 1B-D). This analysis was expanded to include other routes of vector administration and other markers of systemic toxicity. LV-hFIX delivered by either intraportal vein, intra-tail vein, splenic or direct liver routes did not induce any significant increase in serum sGPT (FIG. 1E), creatinine (FIG. 1F), alkaline phosphate (FIG. 1G) or albumin (FIG. 1H) levels. For all test groups, levels of these markers of liver, kidney and cardiac toxicity remained in the normal range at both early and late time points following gene transfer and were indistinguishable from PBS injected control animals. Similar results were obtained with C57Bl/6 mice. These results indicate that lentiviral vector gene transfer did not induce or require vector-induced cytopathology.

In a second study, Swiss nude mice were dosed with either $1.5\times10^8$ transducing units (TU) (3 µg) or $1.5\times10^9$ TU (30 µg) of LV-hFIX into the portal vein, and sera were collected at various time points (FIG. 6A). TaqMan PCR analysis of livers of these mice 48 days after vector administration indicated that increasing the vector dose 10-fold produced only a modest increase in vector genomes in the liver (FIG. 6B). The spleens of the LV-hFIX mice were positive for vector genomes, although the vector genome levels were significantly lower than in the liver (FIG. 6C). No significant changes in serum creatine phosphokinase (CPK), creatinine, alkaline phosphatase, or albumin levels were observed at either dose or at any time point after vector administration (FIG. 6D-G). A slight increase in serum glutamic-pyruvic transaminase (sGPT) levels was observed one day after vector administration in the high-dose group (FIG. 6H). However, sGPT levels returned to normal at three days after vector administration. Even on day 1, the peak levels of sGPT in the 30 µg LV-FIX group were within the normal range for mice (<50 IU). Mice that received LV-hFIX by the intraportal route showed average serum hFIX levels of 140 ng/ml (n=4). Serum hFIX levels were lower in mice that received LV-hFIX by the tail vein route, with average serum levels of 70 ng hFIX/ml (n=4). Serum markers were all in the normal range for both groups of mice.

Figure 2B:
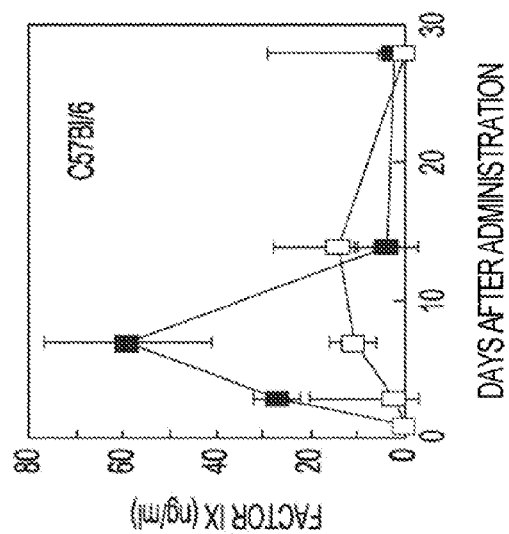
Figure 2C:
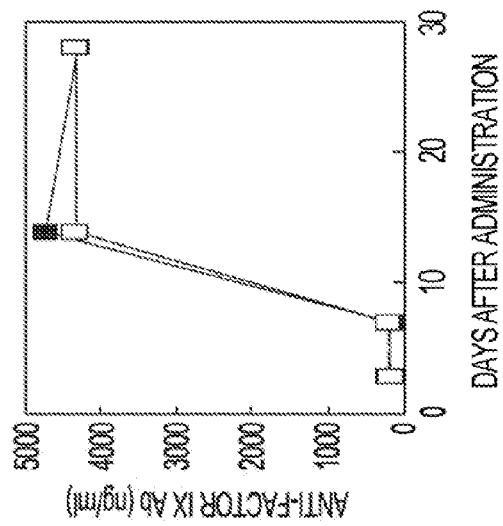

To determine if LV-hFIX gene delivery was mouse strain dependent, $2\times10^8$ TU of LV-hFIX was administered to the tail vein or portal vein of Swiss nude and C57BL/6 mice and the serum hFIX levels measured. The kinetics of hFIX expression in C57Bl6 mice following portal vein administration of LV-hFIX (FIG. 2B) was faster than that observed in the Swiss nudes (FIG. 2A), however, serum hFIX protein levels dropped by 14 days. The levels of hFIX in the C57BL/6 mice that received the vector via the tail vein were lower and were also diminished over time. As the C57Bl6 mice are immunocompetent, one explanation for the disappearance of hFIX protein might be the induction of an anti-human hFIX humoral immune response in the mice. Indeed, high titer anti-hFIX antibodies were detected in the serum of the LV-hFIX transduced C57BL/6 mice and the kinetics of the appearance of these antibodies corresponded with the loss of serum hFIX expression (FIG. 2C). Despite the induction of an anti-hFIX response, there were no apparent changes in serum toxicity marker levels in these mice.

Figure 3B:
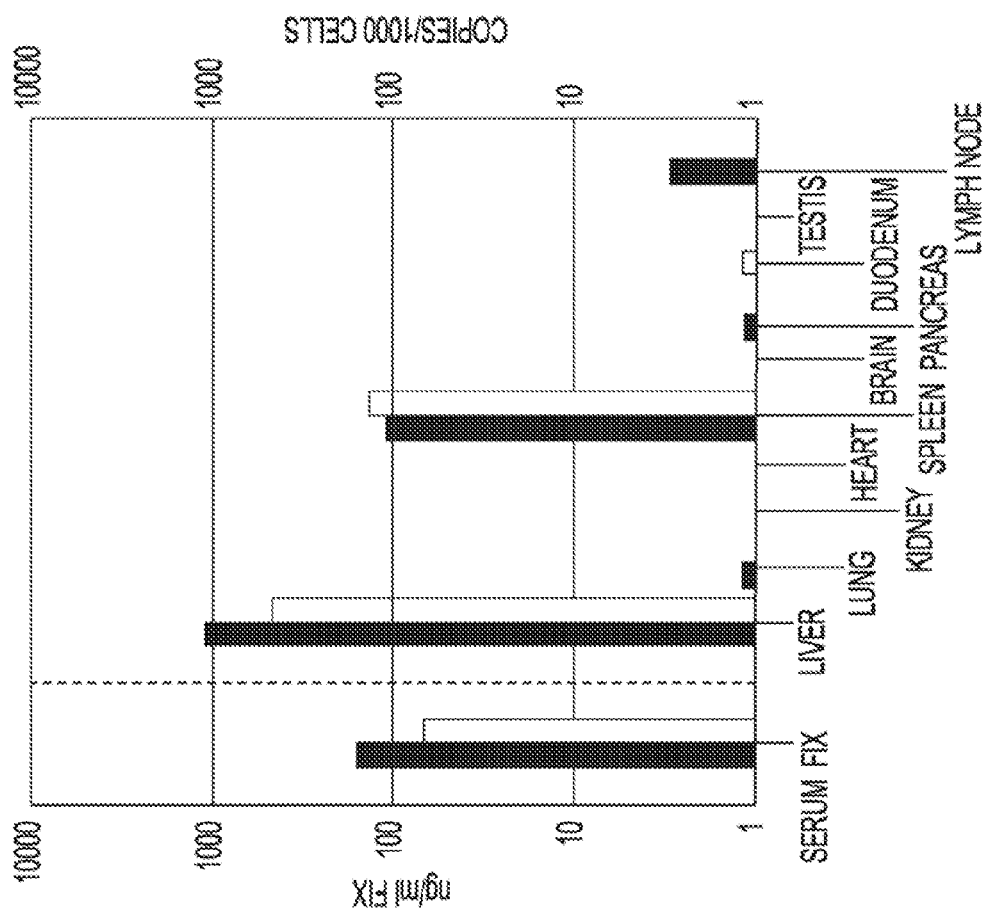
FIGS. 3A-3B are bar graphs showing biodistribution and quantification of lentiviral genomes in LV-hFIX mice. Groups of 4 adult Swiss nude mice received $2\times10^8$ TU of LV-hFIX by either portal vein (closed bars) or tail vein (open bars) and 48 days after gene transfer, the following tissues were collected: liver, lung, kidney, heart, spleen, brain, pancreas, duodenum, testis and lymph node. DNA was extracted and was analyzed by TaqMan PCR for the presence of Lentiviral genomes.
Figure 3A:
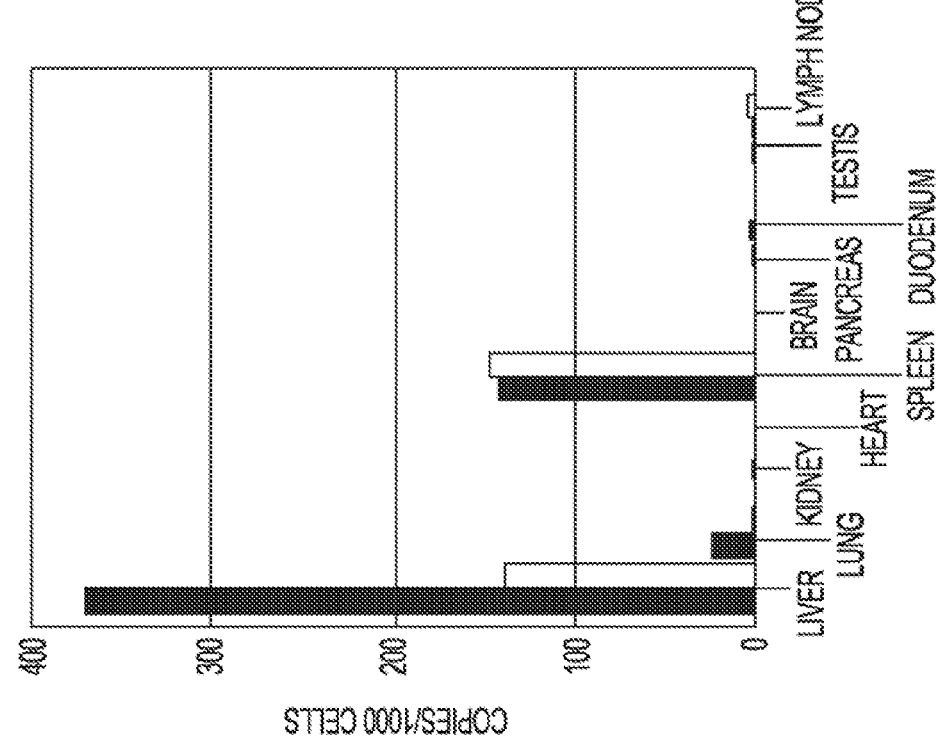

To determine the target organs of the LV-hFIX, DNA was isolated from various tissues from LV-hFIX transduced mice and the LV copy number/1000 cells determined by quantitative PCR (FIG. 3A). In mice that received the LV-hFIX by the portal vein route the liver was the predominant tissue transduced (FIG. 3A, black bars). The livers of these mice demonstrated approximately 350 vector genomes/1000 cells. The spleen demonstrated approximately ½ of number of vector genomes observed in the liver with 150 vector genomes/1000 cells. A very minor fraction of the vector genomes were present in the lung. All other tissues sampled, kidney, heart, brain, pancreas, duodenum, testis, mesenteric lymph nodes, possessed less than 0.2% of the total vector genomes detected with most of the samples being negative, A similar analysis was performed with mice that received the LV-hFIX by the tail vein route. Again the liver and spleen were the primary tissues that were transduced by the vector (FIG. 3A, white bars). Both of these tissues possessed approximately 150 vector genomes/1000 cells. All other tissues demonstrated minimal number of vector genomes.

The number of lentiviral vector genomes in the liver appeared to correlate with the serum hFIX levels. In FIG. 3B is shown the quantification of vector genomes for two individual mice that received vector by either the portal vein (FIG. 3B, black bars) or tail vein (FIG. 3B white bars). In the portal vein LV-hFIX mouse that expressed 159 ng hFIX/ml, 1085 lentiviral vector genome copies/1000 liver cells were detected. The tail vein LV-hFIX mice expressed approximately 2 fold lower levels of hFIX (67 ng hFIX/ml) and possessed approximately 2 fold lower lentiviral vector genome copies in the liver cells (465 copies/1000 cells). By contrast these two mice demonstrated similar levels of vector genomes in their spleens. No other tissue in these mice expressed significant number of lentiviral vector genomes. These data suggested that the liver might be the primary site of hFIX expression.

Figure 4A:
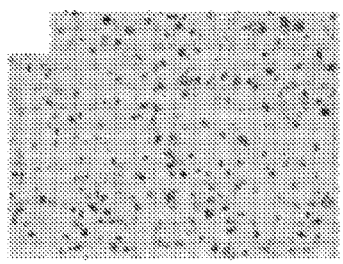
FIGS. 4A-4I are photomicrographs showing expression of hFIX in the liver and spleen following LV-hFIX gene transfer. Livers and spleens of LV-hFIX transduced mice were analyzed by immunohistochemistry for hFIX expression 48 days following portal vein or tail vein delivery of $2\times10^8$ TU of LV-hFIX. Liver sections from PBS control (FIG. 4A), LV-hFIX portal vein (FIG. 4B) and LV-hFIX tail vein (FIG. 4C) mice are shown stained by anti-hFIX immunohistochemistry. Mouse liver sections were also stained with hematoxylin and eosin (H and E): PBS (FIG. 4D), portal vein (FIG. 4E), tail vein (FIG. 4F). Sections from spleens of PBS control (FIG. 4G), LV-hFIX portal vein (FIG. 4H) and LV-hFIX tail vein (FIG. 4I) mice are shown stained by anti-hFIX immunohistochemistry.
Figure 4B:
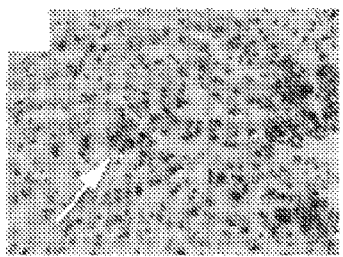

To demonstrate hFIX protein expression in the livers of the LV-hFIX mice, hFIX immunohistochemistry was performed on livers from animals that received LV-hFIX by portal vein and tail vein 48 days following gene transfer. The staining procedure used here did not cross react with the endogenous murine FIX protein as demonstrated in the PBS control mice, which did not exhibit significant HRP (brown) staining (FIG. 4A). In contrast, 25% to 35% of the liver cells in the portal vein LV-hFIX mice stained positive for hFIX (FIG. 4B, arrows). Staining was localized to both hepatocytes and liver sinusoidal cells. The hepatocytic staining was patchy and moderate (FIG. 4B) while the liver sinuses stained strongly positive for hFIX. Liver sections were stained with Perl's Prussian blue stain for Kupffer cells or with anti-CD34 to indicate endothelial cells that make up the sinuses. Endothelial cells in the liver sinuses stained strongly positive for hFIX. Some Kupffer cells also stained positive for hFIX.

Figure 4C:
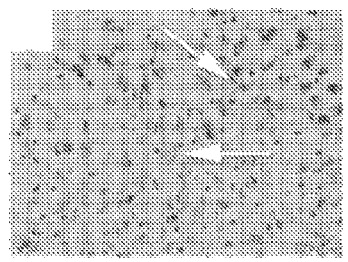
Figure 4D:
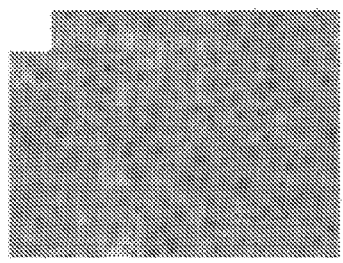
Figure 4E:
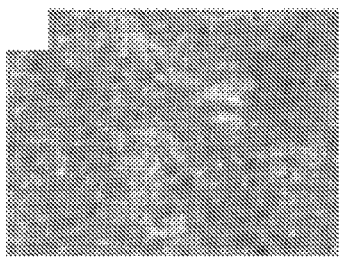
Figure 4F:
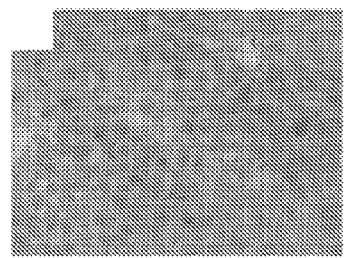

Mice that received LV-hFIX by tail vein administration demonstrated reduced hFIX staining in the liver relative to the portal vein treated animals with approximately 5% to 15% of the liver cells staining positive for hFIX. The intensity of hFIX staining was also reduced in both hepatocytes and liver sinuses (FIG. 4C, arrow). Hematoxylin and eosin staining of liver sections from the LV-hFIX transduced animals showed no signs of vector mediated liver toxicity (FIGS. 4E and F) compared to PBS control mice (FIG. 4D), consistent with the serum marker results.

Figure 4G:
Figure 4H:
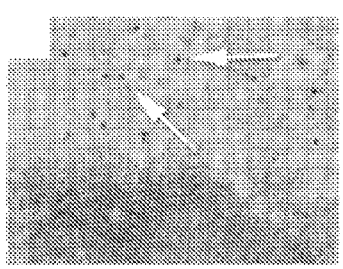
Figure 4I:
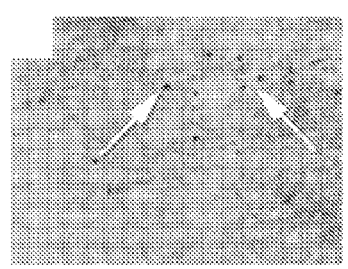

The quantitative PCR analysis of vector genomes indicated that the spleen was an important site of transduction for the LV-hFIX by both routes of administration. Immunohistochemistry staining for hFIX was performed on spleens from animals that received LV-hFIX by portal vein and tail vein 48 days following gene transfer. As expected no hFIX staining was observed in the spleens of the PBS control mice (FIG. 4G). In the tail vein LV-hFIX mice, however, approximately 10% of the cells of the spleen stained positive for hFIX staining (FIG. 4I), and approximately 10% of the splenocytes in the tail vein LV-hFIX mice stained positive for hFIX (FIG. 4I). In both sets of animals, splenic hFIX staining appeared to be predominantly in lymphocytic cells. As Swiss nude mice are T cell deficient, these cells are likely to be B cells.

This study was repeated by delivering $4 \times 10^8$ TU of a LV-GFP vector into the tail vein of C57BL/6 mice. The presence of GFP expression in immune cells (i.e., the T cells, B cells, and antigen-presenting cells) was determined by fluorescence-activated cell sorting (FACS) five days after vector administration. The results are shown in Table 1. Overall, 2.6% of the splenocytes expressed GFP. The majority of these GFP+ cells were MHC class II positive, with approximately half being B cells. Some GFP expression was also observed in T cells. The transduction and expression of the transgene in antigen-presenting cells in C57B mice may be responsible for the induction of the robust anti-hFIX humoral immune response observed in these immunocompetent mice following LV-hFIX administration.

TABLE 1

| | Transgene expression in splenocytes* | | | |
|---|---|---|---|---|
| | Treatment | | | |
| | GFP+ | GFP+/CD3+ | GFP+/B220+ | GFP+/MHC II+ |
| Control | 0.32% | 0.03% | 0.13% | 0.31% |
| LV-GFP | 2.61% | 0.37% | 1.32% | 2.44% |

*LV-GFP ($4 \times 10^6$ TU) was administered into the tail vein of C57BL/6 mice (three mice/group). The spleens were harvested five days later, and the splenocytes were stained with antibodies directed to T cells (CD3), B cells (B220), and MHC class II-positive cells. The cells were then analyzed for immunofluorescence by FACS.

Figures 7A, 7B, 7C, 7D:
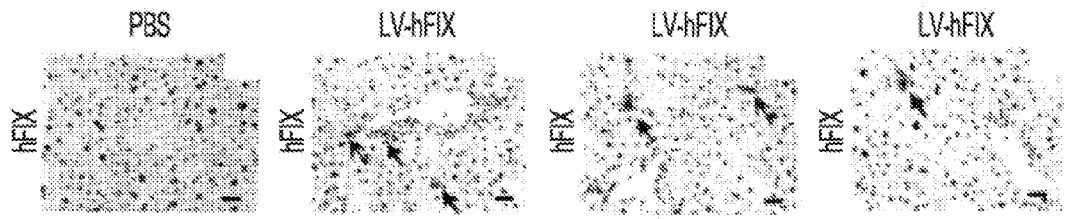
FIGS. 7A-7L are photomicrographs showing expression of hFIX in the liver after LV-hFIX gene transfer. Livers of three mice were analyzed by immunohistochemistry for hFIX expression 122 days after portal vein delivery of LV-hFIX ($1.5\times10^9$ TU). Liver sections from PBS control (FIG. 7A) and LV-hFIX portal vein mice (FIG. 7B-FIG. 7D) are shown stained by hFIX immunohistochemistry. Liver sections from PBS control (FIG. 7E) or LV-hFIX-treated mice (FIG. 7F-FIG. 7H) were stained using an anti-CD31 (PECAM-1) antibody to identify the endothelial cells. Mouse liver sections were also stained with H & E: PBS (FIG. 7I), LV-hFIX (FIG. 7F-FIG. 7L). Scale bar, 10 µm.
Figures 7E, 7F, 7G, 7H:
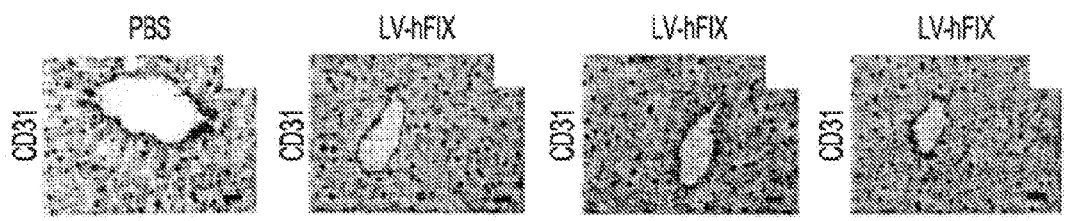
Figures 7I, 7J, 7K, 7L:
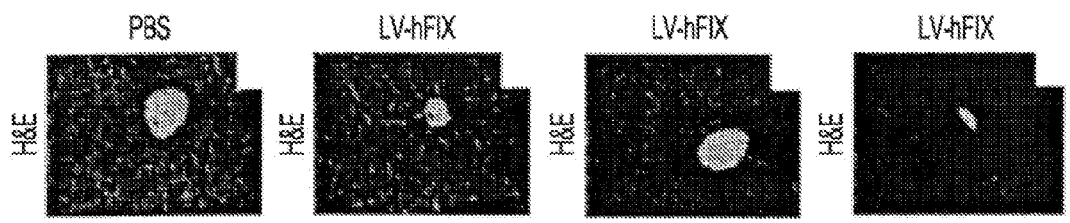

In addition, Immunohistochemistry for hFIX was performed on livers from animals that received LV-hFIX by portal vein 122 days after gene transfer. The staining procedure used here did not cross-react with the endogenous murine FIX protein, as demonstrated in the PBS control liver, which did not exhibit any horseradish peroxidase (HRP)-positive (brown) staining (FIG. 7A). In contrast, 4% of the liver cells in the LV-hFIX-transduced mice stained positively for hFIX (FIG. 7B-D, arrows). As demonstrated in the three representative sections of FIGS. 7B-D, hFIX-positive cells were observed in most sections examined. Liver sections were stained with anti-CD31 (PECAM-1) to mark the endothelial cells that line the liver sinuses. The pattern of staining of these cells (FIG. 7E-H) was very different from that seen with the hFIX-stained sections. Although the occasional endothelial cell (empty arrow) stained positively for hFIX, staining was predominantly localized to the hepatocytes (filled arrows), as indicated by the morphology of the hFIX-positive cells and the distinct pattern of staining observed with the hFIX and CD31 immunohistochemical stains. A similar pattern of gene expression was also observed following vascular delivery of a LV-GFP vector. Hematoxylin and eosin (H & E) staining of sections from the LV-hFIX-transduced mice indicated normal liver architecture and the absence of inflammatory cell infiltrates in the control and gene-modified mice (FIG. 7J-L), consistent with the normal serum marker levels.

Figure 5A:
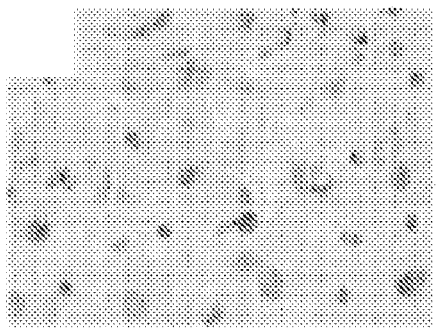
FIGS. 5A-F are photomicrographs showing expression of hFIX and PCNA in the liver following LV-hFIX gene transfer. Serial liver sections from PBS control (FIG. 5A, FIG. 5C, FIG. 5E) and LV-hFIX portal vein (FIG. 5B, FIG. 5D, FIG. 5F) mice for were stained for PCNA (FIG. 5A and FIG. 5B) or hFIX (FIG. 5C and FIG. 5D) expression 3 days following portal vein delivery of $2\times10^8$ TU of LV-hFIX. Sections were also stained with H and E (FIG. 5E and FIG. 5F). PCNA staining is denoted by the black arrow and hFIX staining is denoted by the white arrow.
Figure 5B:
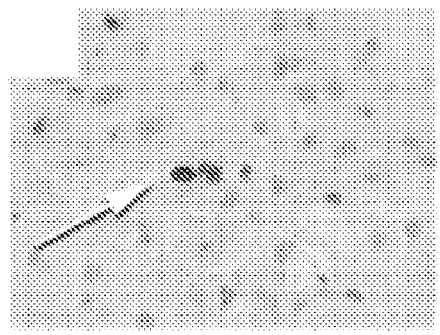
Figure 8A:
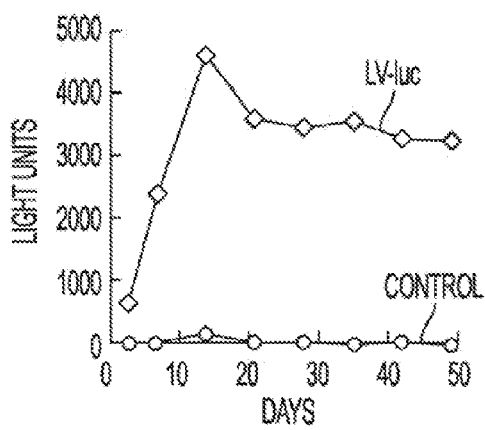
FIG. 8A is a graph showing the kinetics of LV-luciferase (LV-luc) gene transfer. Adult Swiss nude mice received $2\times10^8$ TU of LV-luc into the portal vein, and the expression of luciferase was monitored in the mice over time (three mice/group).
Figure 8B:
FIG. 8B is a typical image of a pair of LV-luc-treated and control mice (as in FIG. 8A) 14 days after vector delivery, with the primary organs of LV transduction, the liver and spleen, indicated.

The kinetics of gene expression after vector administration was examined by injecting $2\times10^8$ TU of a lentiviral vector encoding the luciferase gene (LV-Luc) into the portal vein of adult mice. At various time points following vector administration, luciferase gene expression was quantified by administering luciferin to the mice and imaging with a Xenogen (Alameda, Calif.) IVIS camera system. As soon as three days following LV-Luc administration, luciferase gene expression could be detected in the liver and spleen (FIG. 5A). Gene expression stabilized after two to three weeks and was stable over the course of the experiment. A typical image of mice that received either the LV-Luc or no vector is shown two weeks after vector administration (FIG. 8B). The luminescence observed in the hindlimbs was not consistently observed with subsequent imaging and may either represent background signal or a low-level signal from transduced bone marrow in the leg.

Figure 5C:
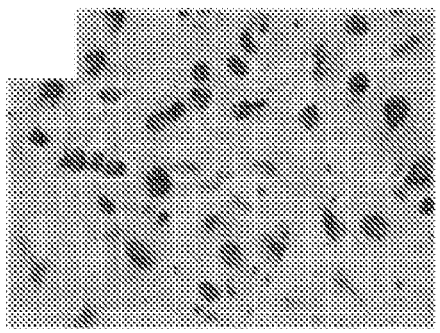
Figure 5D:
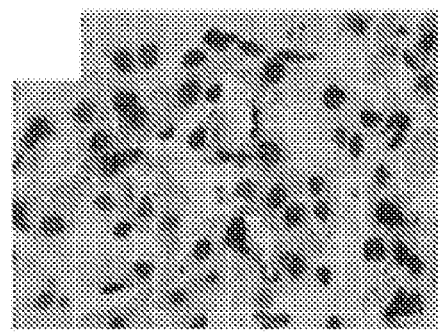
Figure 5E:
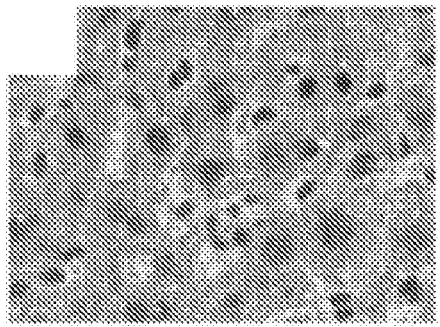
Figure 5F:
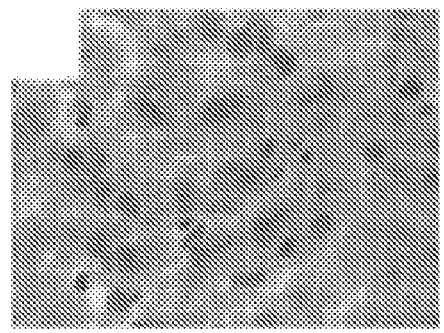

It has been suggested that lentiviral vectors require DNA replication to transduce hepatocytes[14]. To address this question, liver sections taken from mice that received $2\times10^8$ TU of LV-hFIX via the portal vein 3 days following gene transfer were stained for the expression of PCNA. PCNA is a transcription factor that is upregulated during the $G_1$/S phase transition and through DNA replication. In the PBS control and LV-hFIX transduced mice, 0.3-0.5% of the hepatocytes stained positive for PCNA 3 days following portal vein delivery of Lentivirus (FIGS. 5A and B). In contrast, approximately 10-15% of liver cells in the LV-hFIX treated mouse stained positive for hFIX (FIG. 5D). No hFIX expression was observed in serial sections in the liver from the PBS control mouse (FIG. 5C). From this analysis, it appears that vascular delivery of lentiviral vectors does not induce hepatocellular cytopathology or hepatic cell division (FIGS. 5E and F). Furthermore, the transduction of hepatocytes by lentiviral vector does not require cell division.

Figure 9A:
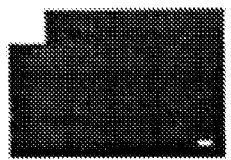
FIGS. 9A-L demonstrate that lentiviral transduction of the liver does not require cell proliferation.
Figure 9B:
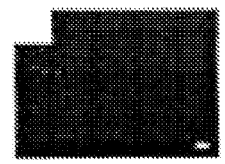
Figure 9C:
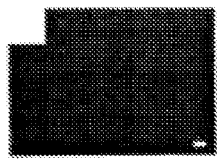
Figure 9D:
Figure 9E:
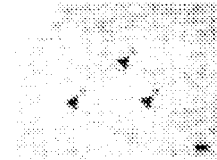
Figure 9F:
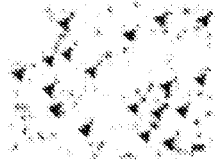
Figure 9G:
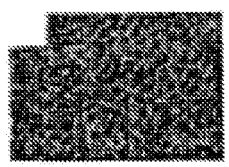
Figure 9H:
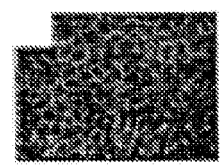
Figure 9I:
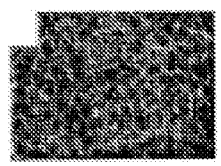
Figure 9J:
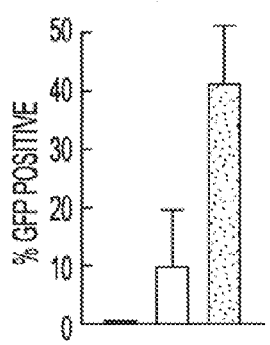
Figure 9K:
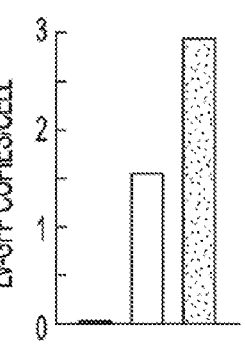
Figure 9L:
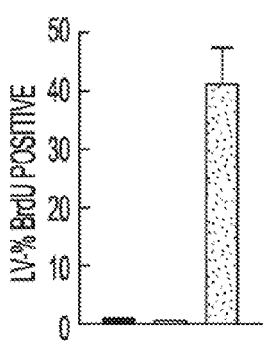

To further assess whether hepatocyte cell division is required for lentiviral vector-mediated gene transfer, a partial hepatectomy was performed on mice before portal vein administration of the LV-GFP vector. Liver sections from these mice were compared to those from nonhepatectomized LV-GFP-transduced mice. Although no GFP expression was observed in control mice (FIG. 9A), it was readily detected in the livers of nonhepatectomized mice that received LV-GFP (FIG. 9B). In mice that received a partial hepatectomy (FIG. 9C), the transduction efficiency was higher, and transduced cells were larger in size and brighter than in the nonhepatectomized mice. Quantification of GFP expression indicated that ~10% of the hepatocytes expressed GFP in the LV-GFP mice while ~40% of liver cells in the LV-GFP transduced mice that had been hepatectomized expressed GFP (FIG. 9J). Approximately 2 vector copies/cell were detected in the control LVGFP livers, and the hepatectomized animals showed approximately 3 vector genomes/cell (FIG. 9K). In a subset of the mice, 5-bromo-2'-deoxyuridine (BrdU) was administered for seven days after vector administration to identify the cells that had proliferated. Similar levels of BrdU-positive cells were observed in the nonhepatectomized LV-GFP and PBS control mice (<1%; FIG. 9D, E, arrows). As expected, the number of BrdU-positive cells was increased in the hepatectomized LV-GFP mice (>40%) (FIG. 9F). Analysis of H & E-stained liver sections from these mice indicated that there was no vector-mediated cytopathology or inflammatory infiltrates (FIG. 9H), and the transduced liver sections were comparable to the normal controls (FIG. 9G).

Discussion

Lentiviral vectors have been shown to transduce a variety of cell types both in vitro and in vivo, including cell types that are normally quiescent. As shown here, vascular administration of a VSV-G pseudotyped $3^{rd}$ generation lentiviral vector encoding human factor IX resulted in the significant transduction of hepatocytes and liver sinus endothelial cells and produced therapeutic levels of hFIX in the serum of mice. Up to 12-35% of the liver cells were observed to express hFIX, depending on route of administration, and maximal hFIX serum levels were 200 ng hFIX/ml following portal vein administration of $1.5\times10^9$ TU of LV-hFIX.

Serum hFIX eves reached 4% of normal levels following vascular lentiviral-mediated hFIX gene transfer, and remained stable for months following vector administration. Human FIX levels as low as 1-2% of normal are considered sufficient to achieve a therapeutic effect. A level of 200 ng/ml would put a severe hemophiliac into the moderate range for FIX.

No evidence of concomitant local or systemic cytopathology was observed in the treated mice. No induction of hepatocytic DNA replication was detected following vector administration, and there was no apparent correlation between the cycling hepatocytes and those that expressed hFIX.

Park et al. reported that doses of $8\text{-}10^8$ TU of LV-LacZ vector were required to achieve significant transduction of the liver following portal vein administration of vector[14]. In addition, Park et al. reported that lentivirus vector at these doses mediated significant hepatocellular toxicity and that 74% (20/27) of mice died following administration of $8\text{-}10\times10^8$ TU of LV-LacZ[14]. This level of toxicity has not been observed in the studies described herein or in studies employing LV-hFIX doses up to $4\times10^8$ TU and LV-LacZ doses up to $8\times10^8$ TU. Park et al. also reported that over 100 µg of p24 per dose of $2^{nd}$ generation LV-hFIX was required to achieve therapeutic serum levels of hFIX[13]. These amounts of virus (p24 equivalents) were 10- to 25-fold higher than those required in the current study.

Park et al. also reported minimal lentivirus vector transduction of the liver in the absence of hepatocyte replication. The transduction efficiency was improved when vector was administered following a partial hepatectomy of the animals. In the current study, using a similar dose (p24 equivalents) of lentiviral vector, approximately 4% of the liver cells in the LV-treated groups expressed hFIX, as determined by immunohistochemistry. Delivery of a lentiviral vector encoding GFP resulted in up to 10% of the hepatocytes expressing FP.

Vascular delivery of lentiviral vector encoding hFIX in C571B/6 mice resulted in a robust humoral response to hFIX. This was also accompanied by a robust anti-VSV-G envelope-directed response. Vascular administration of lentiviral vectors results in the transduction of the spleen and bone marrow. In addition, transgene expression from a cytomegalovirus (CMV) promoter-driven cassette can be readily detected in splenic antigen-presenting cells, B cells, and to a lesser extent T cells, following vascular delivery of lentiviral vector. However, this can be averted through the use of a liver-specific promoter to drive transgene expression. This would eliminate the antigen-presenting cell-driven immune response to the lentiviral vector-encoded transgene.

These results indicate that lentiviral vectors can transduce a variety of cells in the liver to express and secrete the clotting factor, Factor IX, without apparent hepatocellular cytopathology and without requiring cell division. This vector's large coding capacity and its ability to transduce the cells of the liver, the body's largest secretory organ, supports the use of this vector in the treatment of a variety of genetic diseases.

Materials and Methods

Vector constructs and vector production: The LV-hFIX expression construct, pRRL-sin-CMV-hFIX-PRE, a self-inactivating vector, was constructed by cloning the hFIX cDNA[15], driven by the CMV IE enhancer/promoter and containing the SV40 poly-adenylation signal sequence, was introduced into a pRRL-based lentivirus transfer vector described previously[6,7] using standard cloning techniques. The woodchuck hepatitis b virus post-transcriptional regulatory element (WPRE) was introduced 5' of the 3' LTR of the vector[16].

The method of production of the 3rd generation lentiviral vector has also been described[6] with some modifications. Briefly, vectors were produced by transient transfection of 293T cells. A total of 21.0 μg of plasmid DNA was used for the transfection of one 10 cm dish: 3.5 μg of the envelope plasmid, pMD.G, 5.0 μg of packaging plasmid, pMDLg/p.rre, 2.5 μg of pRSV-REV and 10 μg of transfer vector plasmid (pRRL-sin-CMV-hFIX-PRE). After harvesting, vector supernatants were cleared by low speed centrifugation, and filtered through 0.22-μm-pore-size cellulose acetate filters. Vectors were then concentrated by high speed centrifugation using a SW-28 rotor (Beckman, Fullerton, Calif.) at 19,500 r.p.m. for 140 minutes. Immediately after centrifugation, the supernatant was removed and the pellet resuspended in PBS w/o $Ca^{++}$ and $Mg^{++}$. The vector was then frozen and stored at −80° C.

Transducing activity was determined in vitro by infecting $1 \times 10^5$ HeLa cells using serial dilutions of vector preparations expressing either hFIX or eGFP in a six-well plate in the presence of Polybrene (8 μg/ml; Sigma, St. Louis Mo.). Following a 16 hour infection, the vector supernatant was removed and fresh media was added. Forty eight hours later, the media was removed again, and fresh media added. After twenty four hours, the supernatant from cells transduced with LV-hFIX was collected to measure hFIX expression levels by ELISA. Cells that were transduced with Lenti-eGFP were collected analyzed by FACS for eGFP transgene expression. DNA was also extracted from Lentivirus transduced cells and analyzed for the presence of Lentiviral vector genomes as determined by TaqMan PCR analyses. Viral p24 antigen concentration was determined by immunocapture (Alliance; DuPont-NEN, Boston, Mass.). The lentiviral vector preparations had an infectivity of $5 \times 10^7$-$1 \times 10^8$ TU/μg p24 Gag antigen.

Animal procedures: C57BL/6 and NIH Swiss nude mice were obtained from Taconic Laboratories (Germantown, N.Y.) and housed under barrier conditions. 6-8 week old adult mice were administered 100 μl of Lentivirus (4 μg p24) via portal vein or tail vein, intrasplenic or direct liver. For portal vein injections, cannulations were performed 2 days before injection. At various time points following injection, serum was collected via retro-orbital bleeding. Mice were sacrificed 48 days following injection. The following tissues were fresh frozen and subsequently analyzed by TaqMan DNA-PCR or processed for histological analyses: liver, lung, kidney, heart, spleen, brain, pancreas, duodenum, testis and mesenteric lymph node.

Antigen assay for human Factor IX: Mouse serum was analyzed for total human Factor IX antigen by ELISA. Briefly, 96-well plates (Costar) were coated with 2 μg/ml of monoclonal anti-human Factor IX antibody (Boehringer-Mannheim) in 0.1 M carbonate buffer (pH 9.6) at 4° C. overnight. Plates were washed 5× in BBST (BBS containing 0.025% Tween-20). Plates were blocked in 1% (w/v) nonfat dry milk in BBS (89 mM boric acid, 90 mM NaCl, pH 8.3) for 2 hours at room temperature. Samples were diluted in 1% (w/v) nonfat dry milk in BBS at a 1:4 dilution. 50 μl of sample was incubated on plate for 2 hours at room temperature. Plates were washed 5× with BBST and incubated with HRP conjugated goat anti-human factor IX antibody (1:100) (Affinity Biologicals, Hamilton, Canada) for 1.5 hours at room temperature. Plates were washed and 50 μl of p-nitrophenyl phosphate substrate solution was added. The reaction was stopped with 50 μl 2M sulfuric acid and read at 490 nm with a microplate reader (Molecular Devices, Menlo Park, Calif.). Factor IX levels were calculated based on a standard curve generated from a serial dilution of purified human Factor IX standard (Calbiochem, La Jolla, Calif.) diluted in 25% control mouse plasma. The values are expressed in ng/ml.

Antibodies to hFIX: Anti-hFIX anti bodies were detected by ELISA. Briefly, 96 well plates were coated with human Factor IX (Calbiochem, La Jolla, Calif.). Serum samples were incubated on plate at 1:5 or 1:10 dilutions. Horseradish peroxidase conjugated goat anti-mouse IgG was used as the detection antibody. Plates were developed using o-Phenylenediamine dihydrochloride (OPD) substrate. The values were determined based on a standard curve using a monoclonal anti-human factor IX antibody (Boehringer Mannheim, Indianapolis, Ind.).

Serum Analyses: Serum samples were collected from animals before or various time points after gene delivery. Serum glutamine pyruvate transaminase (sGPT), alkaline phosphatase and creatinine assays were performed using kits obtained from Sigma (St. Louis, Mo.). The values are expressed in international units/ml.

Histological analyses: Liver and spleen tissues were collected from the mice at 48 days after administration and fresh frozen. 8 μm sections were cut and stained with hematoxylin and eosin.

Factor IX Immunohistochemistry: Frozen sections were also processed for Factor IX immunohistochemistry. Briefly, cryosections were fixed for 15 minutes in 1% paraformaldehyde in PBS, pH 7.4 and washed in PBS with 1% BSA. Sections were blocked with normal donkey serum and washed in PBS containing 1% BSA. Sections were then incubated with a sheep anti-human Factor IX antibody (Affinity Biologicals, Hamilton, Ontario, Canada) at 1:1000 diluted in PBS with 1% BSA. The secondary antibody used was a biotinylated donkey anti-sheep IgG (Jackson Immunoresearch Laboratories, West Grove, Pa.) (1:3000) followed by incubation with HRP streptavidin complex. All incubation steps were done at room temperature. Sections were developed with 3'3' Diaminobenzidine (DAB) substrate. Sections were lightly counterstained with hematoxylin.

PCNA immunohistochemistry: 8 μm sections were also stained for PCNA proliferation marker. Sections were fixed in 1% paraformaldehyde. A sheep anti-PCNA primary antibody (Santa Cruz Biotechnology, Santa Cruz, Calif.) was used at 1:50 dilution. Washes were in PBS. The rabbit ImmunoCruz Staining system (Santa Cruz Biotechnology, Santa Cruz, Calif.) was used for secondary antibody staining with streptavidin-HRP and substrate development. Sections were lightly counterstained with hematoxylin. The slides were viewed using a Zeiss microscope at 20×-100× magnification.

BrdU-labeling studies. Mice were cannulated at the portal vein two days before vector administration. Some mice also underwent a two-thirds partial hepatectomy. Six hours before vector administration, BrdU was delivered to all animals by an Alzet Model 2001 osmotic pump (Durect Corp., Cupertino, Calif.). Subsequently, 200 µl of the BrdU solution (40 mg/ml in 0.5 M sodium bicarbonate) were added to an Azlet pump and then implanted subcutaneously to the mice, resulting in BrdU release at 1 µl/h (960 µg BrdU/day). Seven days after vector administration, all animals were killed and their livers harvested. BrdU incorporation was detected using a BrdU labeling and detection kit (Roche GmbH, Basel, Switzerland) as described by the manufacturer.

DNA analyses: DNA was isolated from mouse tissues using the Qiagen tissue DNA extraction kit (Valencia, Calif.). 300-500 ng genomic DNA was analyzed by TaqMan PCR using primers specific to the Lentiviral transfer vector. The primer pair is located upstream of the psi packaging signal in the Lentivirus vector. The following primer set was used to produce a 64 bp amplicon: forward primer, 5'-TGAAAGCGAAAGGGAAACCA-3' (SEQ ID NO: 1) and reverse primer, 5'-CCGTGCGCGCTTCAG-3' (SEQ ID NO: 2). The probe used was 5'-6FAM-AGCTCTCTCGACGCAG-GACTCGGC-TAMRA-3' (SEQ ID NO: 3; Applied Biosystems, Foster City, Calif.). A final reaction volume of 50 µl consisted of TaqMan Universal PCR Master Mix; 0.4 µM each primer; 100 nM of FAM probe (Applied Biosystems, Foster City, Calif.). A plasmid containing the amplicon sequence was, diluted in DNA Hydration buffer and used as a positive control series at 50,000, 5000, 500, 50, 5.0 and 0.5 copies per replicate and run in triplicate. Each reaction was run under the following conditions: 50° C. for 2 minute hold; 95° C. for 10 minute hold, then 40 cycles of 95° C. for 15 seconds and 60° C. for 1 minute in an ABI PRISM 7700 Sequence Detection System unit (Applied Biosystems, Foster City, Calif.). The results were analyzed using the Sequence Detection System (version 1.6.3) software's default settings (baseline 3-15; threshold set to 10× standard deviation of the baseline).

REFERENCES

1. Naldini, L. et al. In vivo gene delivery and stable transduction of nondividing cells by a lentiviral vector. *Science* 272, 263-7 (1996).
2. Naldini, L, Blomer, U., Gage, F., Trono, D. & Verma, I. Efficient transfer, integration, and sustained long-term expression of the transgene in adult rat brains injected with a lentiviral vector. *Proc Natl Acad Sci USA* 93, 11382-8 (1996).
3. Naldini, L. Lentiviruses as gene transfer agents for delivery to non-dividing cells. *Curr Opin Biotechnol* 9, 457-63 (1998).
4. Zufferey, R., Nagy, D., Mandel, R., Naldini, L. & Trono, D. Multiply attenuated lentiviral vector achieves efficient gene delivery in vivo. *Nat Biotechnol* 15, 871-5 (1997).
5. Blomer, U. et al. Highly efficient and sustained gene transfer in adult neurons with a lentivirus vector. *J Virol* 71, 6641-9 (1997).
6. Dull T. et al. A third-generation lentivirus vector with a conditional packaging system. *J Virol* 72, 8463-71 (1998).
7. Zufferey, R. et al. Self-inactivating lentivirus vector for safe and efficient in vivo gene delivery. *J Virol* 72, 9873-80 (1998).
8. Bukovsky, A., Song, J. & L, L. N. Interaction of human immunodeficiency virus-derived vectors with wild-type virus in transduced cells. *J Virol* 73, 7087-92 (1999).
9. Kafri, T., Praag, H. v., Ouyang, L., Gage, F. & Verma, I. A packaging cell line for lentivirus vectors. *J Virol* 73, 576-84 (1999).
10. Curran, M., Kaiser, S., Achacoso, P. & Nolan, G. Efficient transduction of nondividing cells by optimized feline immunodeficiency virus vectors. *Mol Ther* 1, 31-8 (2000).
11. Wang, G. et al. Feline immunodeficiency virus vectors persistently transduce nondividing airway epithelia and correct the cystic fibrosis defect. *J Clin Invest* 104, R55-62 (1999).
12. Wang, X. et al. Efficient and sustained transgene expression in human corneal cells mediated by a lentiviral vector. *Gene Ther* 7, 196-200 (2000).
13. Park, F., Ohashi, K. & Kay, M. Therapeutic levels of human factor VIII and IX using HIV-1-based lentiviral vectors in mouse liver. *Blood* 96, 1173-6 (2000).
14. Park, F., Ohashi, K., Chiu, W., Naldini, L. & Kay, M. Efficient lentiviral transduction of liver requires cell cycling in vivo. *Nat Genet* 24, 49-52 (2000).
15. Snyder, R. et al. Persistent and therapeutic concentrations of human factor IX in mice after hepatic gene transfer of recombinant AAV vectors. *Nat. Genetics* 16, 270-6 (1997).
16. Zufferey, R. Donello, J. Trono, D. & Hope T. Woodchuck hepatitis virus posttranscriptional regulatory element enhances expression of transgenes delivered by retroviral vectors. *J Virol* 73, 2886-92 (1999).
17. Wion, K., Kelly, D., Summerfield, J., Tuddenham, E, & Lawn, R. Distribution of factor VIII mRNA and antigen in human liver and other tissues. *Nature* 317, 726-9 (1985).
18. Ge, Y., Powell, S., Roey, M. V. & McArthur, J. Factors influencing the development of an anti-FIX immune response following administration of AAV-FIX. *Blood* 97(12), 3733-7 (2001).
19. Jooss, K., Yang, Y., Fisher, K. & Wilson, J. Transduction of dendritic cells by DNA viral vectors directs the immune response to transgene products in muscle fibers. *J Virol* 72, 4212-23 (1998).

Example 2

Enhancer1 Augments Expression of Factor VIII in Hepatocytes

Enhancers are composed of smaller elements that can be combined alone or with other elements to produce stronger transcription and varied tissue-specificity. This example describes the creation of a novel liver (hepatocyte) specific synthetic transcriptional enhancer that is capable of increasing expression in a tissue specific manner from a number of promoter elements, and hence represents a more classical "enhancer" that functions with multiple promoters.

The novel transcriptional enhancer was created by synthesizing oligonucleotide binding sites for six liver (hepatocyte) transcription factors and ligating (inking) these sites together in stoichiometric amounts. The six transcription factors, which are described in the literature and known to those skilled in the art, are as follows:

```
DBP
5'-ATTATGTAAG-3';              (SEQ ID NO: 4)

EBP
5'-ATTGCGGCAAT-3';             (SEQ ID NO: 5)

HNF1
5'-AGGTTAATAATTACCAG-3';       (SEQ ID NO: 6)

HNF3
5'-GAYTATTTATTYGGCC-3';        (SEQ ID NO: 7)
```

-continued

```
HNF4
5'-CGCTGGGCAAAGGTCACCTGCCCCT-3';      (SEQ ID NO: 8)
and

HNF6
5'-AATATTGAYTYGAGGC-3';               (SEQ ID NO: 9)
```

(where Y represents either C or T) with compatible "sticky" CGCG overhangs (not shown).

The random arrays of binding sites were cloned upstream of a minimal human albumin promoter (which has minimal basal transcriptional activity on its own) driving expression of GFP in a lentivirus vector construct, thus generating a pool of lentivirus vector plasmids. Viral supernatants were produced from this plasmid pool and used to transduce HuH7 cells (cell culture hepatocytes) at low multiplicity of infections (MOI). After allowing for expression of the vector, cells were sorted based on their GFP expression levels using standard fluorescent cell sorting techniques, enriching a population of cells with elevated GFP expression levels. These cells were grown up as clonal cultures, and DNA was isolated for amplification of the enhancing element by PCR and subsequently sequenced.

These cloned enhancer elements augmented expression levels up to two orders of magnitude over the enhancer-less vector. The cloned enhancer element described here (clone 1.1, or Enhancer 1 or Enh1) is composed of five types of the six initial elements (EBP, HNF1, HNF3, HNF4, HNF6) in the following order and orientation: HNF1 (sense)-HNF3 (sense)-HNF4 (antisense)-HNF1 (antisense)-HNF6 (sense)-EBP (antisense)-HNF4 (antisense). The sequences of Enh1 derived from the hepatocyte elements are in upper case (CGCG sticky ends in italics), with adjacent vector sequences in lower case:

presenting cells thereby initiating or accelerating immunological activity against the therapeutic molecule.

This example describes a novel combination of Enhancer1 with a hepatocyte specific promoter derived from the mouse transthyretin (mTTR) gene. A preferred use of this combination involves driving expression of the human Factor VIII gene for gene therapy applications using a lentivirus-based vector. The novel enhancer element is combined with a promoter element (mTTR) that already contains its own transcriptional enhancer. The mTTR promoter plus endogenous enhancer has been described (R. H. Costa et al, 1986, Molecular and Cellular Biology 6:4697).

Enhancer1 was coned upstream of several (four) different liver specific promoter elements: mTTR promoter, human alpha-1-antitrypsin promoter (hAAT), human albumin minimal promoter, mouse albumin promoter, and transfected into HuH7 cells for expression analysis. The novel enhancer with the mTTR promoter element (consisting of its own enhancer and promoter) was seen to give the highest levels of expression in this assay in a cell type restricted manner. This combination of elements was transferred to the lentivirus system and assayed by transduction of viral supernatants into HuH7 cells. In this assay, the combination of novel enhancer and mTTR promoter was seen to enhance the activity over the mTTR promoter alone by about two fold. Two reporter genes were utilized in this analysis: enhanced green fluorescent protein (plasmid and vector pRRLsinpptEnh1mTTR-EGFP) and human factor VIII (plasmid and vector pRRLsinpptEnh1mTTR-hF8(f8/f9)pre). This novel combination of the synthetic enhancer and the mTTR promoter produced higher levels of expression than previous generations of liver specific promoter or "high-level" ubiquitous

```
  1 gaattcacgc GAGTTAATAA TTACCAGCGC GGGCCAAATA AATAATCCGC(SEQ ID NO: 10)

51 GAGGGGCAGG TGACGTTTGC CCAGCGCGCG CTGGTAATTA TTAACCTCGC

101 GAATATTGAT TCGAGGCCGC GATTGCCGCA ATCGCGAGGG GCAGGTGACC

151 TTTGCCCAGC Gcgcgttcgc cccgcccqa tcq.
```

The Enhancer1 element was subcloned as an EcoRI-PvuII restriction fragment (restriction sites underlined) for further manipulation. It is understood that variations of these elements with respect to number of binding sites, position of binding sites, and orientations of binding sites will also behave similarly or at elevated levels compared to this example. It is also possible that fewer than five of the six types of elements may be sufficient to generate an enhancing element that likewise augments expression.

Example 3

Enhancer1 Combined with mTTR Promoter Provides High-Level Expression of Factor VIII in Hepatocytes This example, like Example 2 above, addresses the problem of obtaining adequate gene expression (therapeutic levels) for gene therapy based applications. It also addresses immunological concerns by directing expression in a tissue specific manner. Previous constructs used ubiquitous promoters that theoretically would allow gene expression in antigen promoters. This combination of enhancer and promoter elements can be used to drive therapeutic levels of factor VIII in vivo.

Example 4

L-F8 Drives Sustained Expression of Factor VIII in a Mouse Hemophilia Model

This example describes a hybrid enhancer and promoter combination, designated L-F8, that can be used to express clotting factors. The combination is suitable for use with a third generation lentiviral expression system. A restriction map of the vector pCCsinL-F8.SMALL.ii.hF8pptpre is shown in FIG. 10.

The L-F8 hybrid comprises an enhancer (L) and a promoter (F8). The enhancer, L, contains two copies of the α-1-microglobulin/bikunin enhancer (Rouet et al., 1992, J. Biol. Chem. 267:20765-20773; Rouet et al., 1995, Nucleic Acids Res. 23:395-404; Rouet et al., 1998, Biochem. J. 334:577-584; III et al., 1997, Blood Coagulation Fibrinolysis 8:S23-S30), and was directly cloned from the vector pCCLsinLSPdxF8pptpre. The promoter used in this hybrid was the human Factor VIII endogenous promoter. An 300 nucleotide fragment, based on a paper that studied the regulation of the Factor VIII promoter (Figueiredo and Brownlee, 1995. J. Biol. Chem. 270:11828-11838), was PCR amplified from genomic DNA and cloned 3' of the enhancer and 5' of the Factor VIII coding sequence.

Figure 10A:
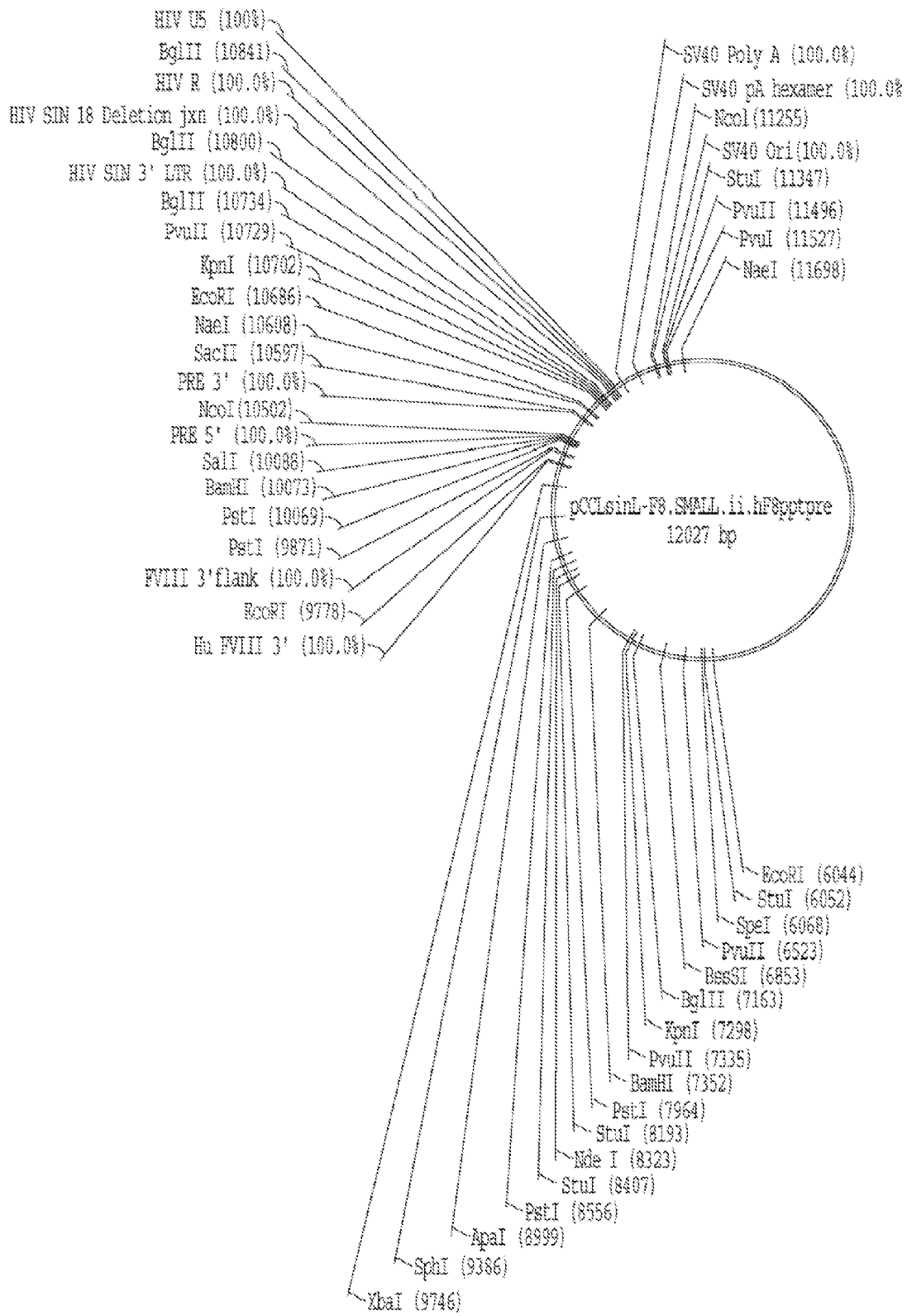
FIGS. 10A-10B provide a restriction map of the vector pCCLsinL-F8.SMALL.ii.hF8pptpre.
Figure 10B:
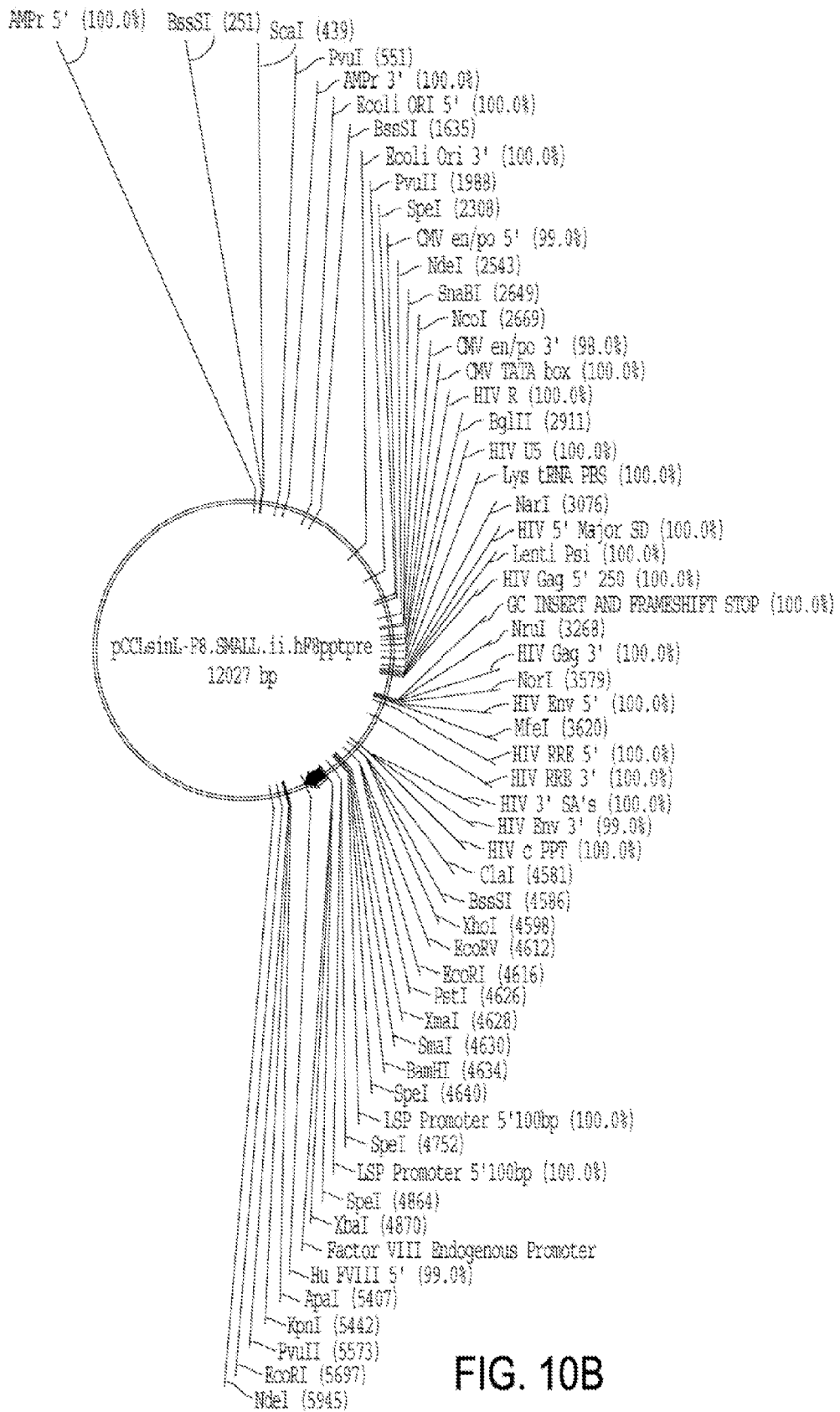

This vector, as shown in FIG. 10, provides sustained expression (>14 days) in the HemoA null mouse in vivo.

Throughout this application, various patents and publications are cited. The contents of these patents and publications is incorporated herein by reference in order to describe more fully the state of the art. In addition, reference is made to techniques commonly understood in the art. Guidance in the application of such techniques can be found in Ausubel et al. eds., 1995, Current Protocols In Molecular Biology, and in Sambrook et al., 1989, Molecular Cloning: A Laboratory Manual, Cold Spring Harbor Laboratory Press, NY, the contents of which are incorporated herein by reference.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fail within the scope of the invention. Such modifications or other embodiments can be practiced without departing from the true scope and spirit of the invention.

What is claimed is:

1. A lentiviral producer cell comprising:
   (a) a gag gene, or a pol gene, or gag and pol genes;
   (b) an env gene; and
   (c) a lentiviral transfer vector that comprises a transgene operably linked to an expression control sequence, wherein the expression control sequence comprises the nucleotide sequences of SEQ ID NO: 5, SEQ ID NO: 6, SEQ ID NO: 7, SEQ ID NO: 8, and SEQ ID NO: 9.

2. The producer cell of claim 1, wherein the expression control sequence comprises the nucleotide sequence of SEQ ID NO: 10.

3. The producer cell of claim 1, wherein the expression control sequence consists of the nucleotide sequence of SEQ ID NO: 10.

4. The producer cell of claim 1, wherein the expression control sequence further comprises a mouse transthyretin (mTTR) promoter.

5. The producer cell of claim 1, wherein the expression control sequence further comprises an α-1-microglobulin/bikunin enhancer and a human factor VIII endogenous promoter (L-F8).

6. The lentiviral producer cell of claim 1, wherein the elements of (a), (b) and (c) are stably integrated into the genome of the lentiviral producer cell.

7. The lentiviral producer cell of claim 1, wherein the lentivirus is a human immunodeficiency virus (HIV).

8. The lentiviral producer cell of claim 7, wherein the HIV is HIV-1.

9. The lentiviral producer cell of claim 1, further comprising a rev gene.

10. The lentiviral producer cell of claim 1, which lacks functional genes selected from tat, vif, vpr, vpu, vpx and nef, or a combination thereof.

11. The lentiviral producer cell of claim 1, wherein the expression control sequence further comprises a liver specific promoter.

12. The lentiviral producer cell of claim 11, wherein the liver specific promoter comprises a mouse transthyretin (mTTR) promoter.

13. The lentiviral producer cell of claim 1, wherein the expression control sequence further comprises an α-1-microglobulin/bikunin enhancer and a human factor VIII endogenous promoter (L-F8).

14. A set of lentiviral vectors comprising:
   (a) a first packaging vector comprising a gag gene, or a pol gene, or gag and pol genes operably linked to an expression control sequence;
   (b) a second packaging vector comprising a heterologous env gene operably linked to an expression control sequence; and
   (c) a lentiviral transfer vector that comprises a transgene operably linked to an expression control sequence;
   wherein the expression control sequence comprises the nucleotide sequences of SEQ ID NO: 5, SEQ ID NO: 6, SEQ ID NO: 7, SEQ ID NO: 8, and SEQ ID NO: 9.

15. The set of claim 14, wherein the expression control sequence comprises the nucleotide sequence of SEQ ID NO: 10.

16. The set of claim 14, wherein the expression control sequence consists of the nucleotide sequence of SEQ ID NO: 10.

17. The set of claim 14, wherein the expression control sequence further comprises a mouse transthyretin (mTTR) promoter.

18. The set of claim 14, wherein the expression control sequence further comprises an α-1-microglobulin/bikunin enhancer and a human factor VIII endogenous promoter (L-F8).

19. The set of claim 14, wherein the transgene encodes a blood clotting factor.

20. The set of claim 14, wherein the transgene encodes human factor IX (hFIX).

21. The set of claim 14, wherein the transgene encodes human factor VIII (hFVIII).

22. The set of claim 14, wherein the lentivirus is a human immunodeficiency virus (HIV).

23. The set of claim 22, wherein the HIV is HIV-1.

24. The set of claim 14, further comprising a fourth vector that comprises a rev gene.

25. The set of claim 14, which lacks functional genes selected from tat, vif, vpr, vpu, vpx and net or a combination thereof.

26. A method of producing a lentiviral producer cell comprising transforming a cell with the set of vectors of claim 14.

27. A method of producing a recombinant lentivirus comprising culturing a producer cell of claim 1 in a medium and recovering recombinant lentivirus from the medium.

28. A method of delivering a transgene to a cell comprising contacting the cell with a recombinant lentivirus produced by the lentiviral producer cell of claim 1 under conditions permitting transformation of the cell.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tgaaagcgaa agggaaacca                                              20

<210> SEQ ID NO 2
<211> LENGTH: 15
<212> TYPE: DNA
<213> ORGANISM: Artificial Sequence
<220> FEATURE:
<223> OTHER INFORMATION: primer

<400> SEQUENCE: 2
ccgtgcgcgc ttcag                                                   15

<210> SEQ ID NO 3
<211> LENGTH: 24
<212> TYPE: DNA
<213> ORGANISM: Artificial Sequence
<220> FEATURE:
<223> OTHER INFORMATION: probe

<400> SEQUENCE: 3
agctctctcg acgcaggact cggc                                         24

<210> SEQ ID NO 4
<211> LENGTH: 10
<212> TYPE: DNA
<213> ORGANISM: Artificial Sequence
<220> FEATURE:
<223> OTHER INFORMATION: transcription factor binding site
      y = c or t

<400> SEQUENCE: 4
attatgtaag                                                         10

<210> SEQ ID NO 5
<211> LENGTH: 11
<212> TYPE: DNA
<213> ORGANISM: Artificial Sequence
<220> FEATURE:
```

```
<223> OTHER INFORMATION: transcription factor binding site
      y = c or t

<400> SEQUENCE: 5
attgcggcaa t                                                            11

<210> SEQ ID NO 6
<211> LENGTH: 17
<212> TYPE: DNA
<213> ORGANISM: Artificial Sequence
<220> FEATURE:
<223> OTHER INFORMATION: transcription factor binding site
      y = c or t

<400> SEQUENCE: 6
aggttaataa ttaccag                                                      17

<210> SEQ ID NO 7
<211> LENGTH: 16
<212> TYPE: DNA
<213> ORGANISM: Artificial Sequence
<220> FEATURE:
<223> OTHER INFORMATION: transcription factor binding site
      y = c or t

<400> SEQUENCE: 7
gaytatttat tyggcc                                                       16

<210> SEQ ID NO 8
<211> LENGTH: 25
<212> TYPE: DNA
<213> ORGANISM: Artificial Sequence
<220> FEATURE:
<223> OTHER INFORMATION: transcription factor binding site
      y = c or t

<400> SEQUENCE: 8
cgctgggcaa aggtcacctg cccct                                             25

<210> SEQ ID NO 9
<211> LENGTH: 16
<212> TYPE: DNA
<213> ORGANISM: Artificial Sequence
<220> FEATURE:
<223> OTHER INFORMATION: transcription factor binding site
      y = c or t

<400> SEQUENCE: 9
aatattgayt ygaggc                                                       16

<210> SEQ ID NO 10
<211> LENGTH: 183
<212> TYPE: DNA
<213> ORGANISM: Artificial Sequence
<220> FEATURE:
<223> OTHER INFORMATION: enhancer element

<400> SEQUENCE: 10
gaattcacgc gagttaataa ttaccagcgc gggccaaata aataatccgc gaggggcagg        60
tgacgtttgc ccagcgcgcg ctggtaatta ttaacctcgc gaatattgat tcgaggccgc       120
gattgccgca atcgcgaggg gcaggtgacc tttgcccagc gcgcgttcgc cccgccccga       180
tcg                                                                    183
```